US012656334B2

(12) United States Patent
Viallat et al.

(10) Patent No.: US 12,656,334 B2
(45) Date of Patent: Jun. 16, 2026

(54) METHOD AND DEVICE FOR DETERMINING RED BLOOD CELLS DEFORMABILITY

(71) Applicants:CENTRE NATIONAL DE LA RECHERCHE SCIENTIFIQUE, Paris (FR); INSTITUT NATIONAL DE LA SANTE ET DE LA RECHERCHE MEDICALE (INSERM), Paris (FR); ASSISTANCE PUBLIQUE - HOPITAUX DE MARSEILLE, Marseilles Cedex (FR); AIX-MARSEILLE UNIVERSITE, Marseilles (FR)

(72) Inventors: Annie Viallat, Marseilles (FR); Emmanuele Helfer, Marseilles (FR); Catherine Badens, Marseilles (FR); Scott Atwell, Saint Germain en Laye (FR); Anne Charrier, Marseilles (FR)

(73) Assignees: Centre National De La Recherche Scientifique, Paris (FR); Institut National De La Sante Et De La Recherche Medicale (Inserm), Paris (FR); Assistance Publique—Hôpitaux de Marseille, Marseille Cedex (FR); Aix-Marseille Université, Marseilles (FR)

( * ) Notice: Subject to any disclaimer, the term of this patent is extended or adjusted under 35 U.S.C. 154(b) by 1035 days.

(21) Appl. No.: 17/729,539

(22) Filed: Apr. 26, 2022

(65) Prior Publication Data

US 2022/0341912 A1      Oct. 27, 2022

Related U.S. Application Data

(63) Continuation-in-part of application No. 17/257,405, filed as application No. PCT/EP2019/068626 on Jul. 10, 2019, now abandoned.

(30)      Foreign Application Priority Data

Jul. 10, 2018      (EP) ..................................... 18305914

(51) Int. Cl.
*G01N 33/49*      (2006.01)
*G01N 15/10*      (2024.01)
      (Continued)

(52) U.S. Cl.
CPC ..... *G01N 33/4915* (2013.01); *G01N 15/1429* (2013.01); *G06T 7/0014* (2013.01);
      (Continued)

(58) Field of Classification Search
CPC ........... G01N 33/4915; G01N 15/1429; G01N 2015/103; G01N 15/1433;
      (Continued)

(56)      References Cited

U.S. PATENT DOCUMENTS

| 2002/0141976 A1 | 10/2002 | Fisher et al. | |
| 2006/0119836 A1* | 6/2006 | Ku ......................... | G01N 33/49 356/39 |
| 2011/0289043 A1* | 11/2011 | Suresh .............. | B01L 3/502746 703/2 |

FOREIGN PATENT DOCUMENTS

| EP | 2128613 A1 | 12/2009 | |
| KR | 20160139605 A | * 12/2016 | .......... C12M 1/3492 |

OTHER PUBLICATIONS

Oishi et al., "Continuous and simultaneous measurement of the tank-treading motion of red blood cells and the surrounding flow using translational confocal micro-particle image velocimetry (micro-PIV) with sub-micron resolution," 2012 IOP, Measurement Science and Technology, vol. 23, No. 3. (Year: 2012).*
      (Continued)

*Primary Examiner* — Emily C Terrell
*Assistant Examiner* — Julia Z. Yao
(74) *Attorney, Agent, or Firm* — Scully, Scott, Murphy & Presser, P.C.

(57)      ABSTRACT
The invention is related to a method for measuring the variability of the red blood cells deformability of an indi-
      (Continued)

vidual by determining the amount of red blood cells having a tank-treading motion in a population of red blood cells from a tested blood sample of said individual, and comparing the amount to a reference amount. The determination of the amount of red blood cells having a tank-treading motion is carried out using a visualisation means such as a bright-field microscope.

9 Claims, 8 Drawing Sheets

(51) Int. Cl.

| | |
|---|---|
| *G01N 15/1429* | (2024.01) |
| *G06T 7/00* | (2017.01) |
| *G06T 7/246* | (2017.01) |
| *G16H 10/40* | (2018.01) |
| *G16H 50/20* | (2018.01) |

(52) U.S. Cl.
CPC ............. *G06T 7/246* (2017.01); *G16H 10/40* (2018.01); *G16H 50/20* (2018.01); *G01N 2015/103* (2024.01); *G06T 2207/10016* (2013.01); *G06T 2207/10056* (2013.01); *G06T 2207/30024* (2013.01); *G06T 2207/30241* (2013.01); *G06T 2207/30242* (2013.01)

(58) Field of Classification Search
CPC ..... G01N 2015/012; G01N 2015/1486; G01N 2015/1495; G01N 15/1459; G06T 7/0014; G06T 7/246; G06T 2207/10016; G06T 2207/10056; G06T 2207/30024; G06T 2207/30241; G06T 2207/30242; G16H 10/40; G16H 50/20; G16H 30/40; G06V 2201/03; G06V 2201/07; G06V 20/695
See application file for complete search history.

(56) References Cited

OTHER PUBLICATIONS

Lanotte et al., "A new look at blood shear-thinning," 2016 arXiv, Biological Physics, vol. abs/1608.03730 [online]. Retrieved from the Internet <URL: https://arxiv.org/abs/1608.03730> (Year: 2016).*
Gambhire et al., "High aspect ratio submicron channels using wet etching. Application to the dynamics of red blood cell transiting through biomimetic splenic slits," Small, 2017, 13 (32), pp. 1700967. (Year: 2017).*
International Search Report dated Aug. 22, 2019 issued in PCT/EP2019/068626.
Dobbe et al., "Analyzing Red Blood Cell-Deformability Distributions", Blood Cells, Molecules, and Diseases (May/Jun. 2002), vol. 28, No. 3, pp. 373-384.
Musielak, M., "Red blood cell-deformability measurement: Review of techniques", Clinical Hemorheology and Microcircula (2009), vol. 42, pp. 47-64.
Dupire, J. et al., "Full dynamics of a red blood cell in shear flow", Proceedings of the National Academy of Sciences of the United States of America (Dec. 3, 2012), vol. 109, No. 51, pp. 20808-20813.
Viallat, A. et al., "Red blood cell: from its mechanics to its motion in shearflow", International Journal of Laboratory Hematology (Apr. 18, 2014), vol. 36, No. 3, pp. 237-243.
Dupire, J. et al., "A simple model to understand the effect of membrane shear elasticity and stress-free shape on the motion of red blood cells in shear flow", Soft Matter (Jan. 1, 2015), vol. 11, No. 42, pp. 8372-8382.

* cited by examiner

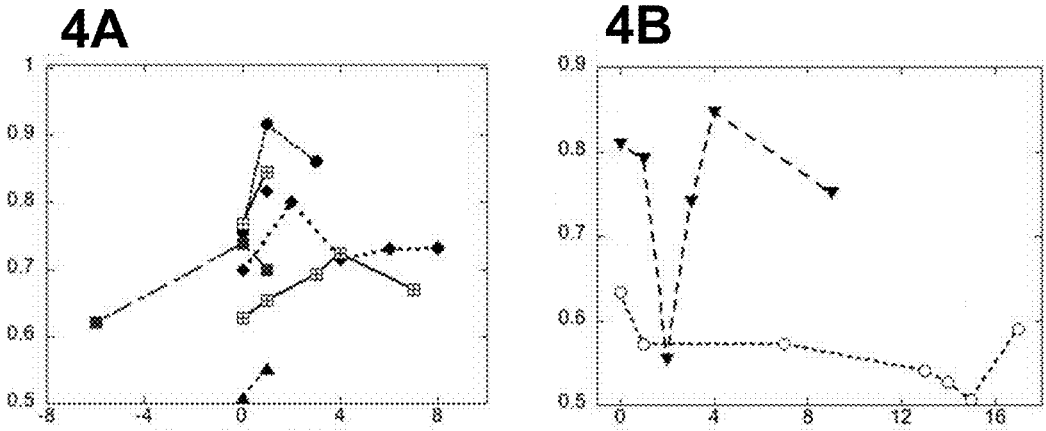
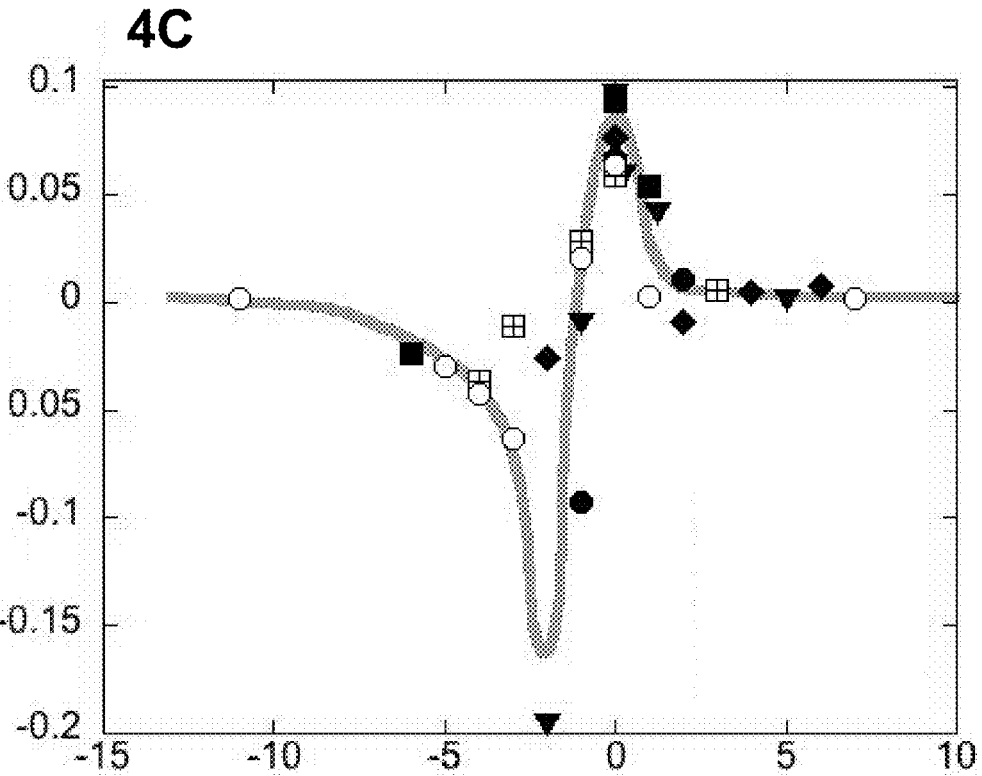
Figures 4A-4C

5A

5B

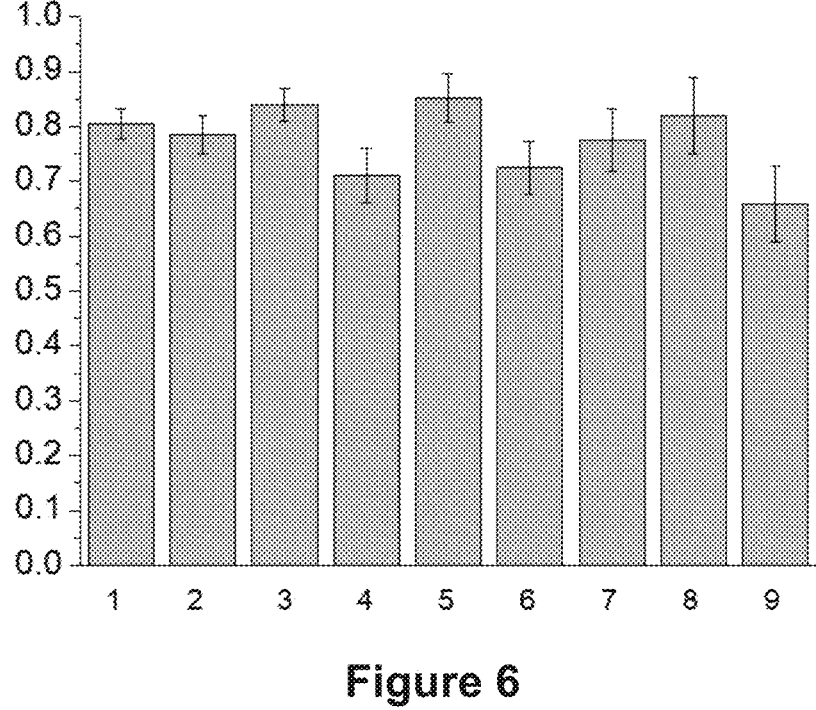
Figure 6
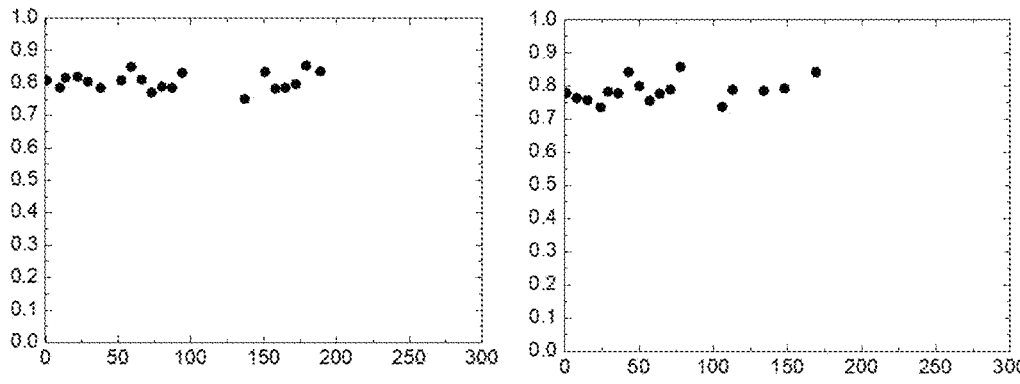
Figure 7                    Figure 8

METHOD AND DEVICE FOR DETERMINING RED BLOOD CELLS DEFORMABILITY

The invention is related to red blood cells deformability and its measurement. The invention is also related to the use of said measurement for applications. The invention is further related to a device for carrying out the said measurement.

The high deformability of red blood cells (RBCs) is an essential element of blood fluidity and is postulated as a major determinant of proper blood microcirculation. Decrease in RBC deformability is observed in a number of acquired or inherited diseases such as diabetes mellitus, sepsis, progression of renal failure, malaria, and sickle cell anaemia (SCD), which are associated with blood circulation disorders. High RBC deformability is not only essential to enable RBCs to deform enough to pass through vessel capillaries smaller than them, but also it plays a crucial indirect role in the interactions between RBCs and vessel walls and between other blood cells, thus affecting blood cell clustering and adhesion, and leading to ischemia, thrombus formation and occlusion in small capillaries.

The deformability of RBCs corresponds to their ability to change shape under a given level of applied stress, without haemolysing, i.e. rupturing. RBC deformability is a complex property, which results from the remarkable combined contribution of several mechanical parameters: i) a shear elastic parameter, the in-plane shear elasticity of the membrane, that resists to deformation under an applied load, ii) the membrane geometry of reference, for which there is no residual shear stress, iii) the viscosities of both membrane and cytoplasm, which control the deformation rate of the cell, and iv) the ratio of the RBC surface area to its volume, which characterizes its capacity to deform by redistributing its volume within the membrane at constant surface area. These parameters are however not easily experimentally measurable. Consequently, the RBCs deformability in a blood sample is often assessed only by a single mechanical parameter, for example, the cell elongation under a high shear stress. But such a parameter is often too simplistic and therefore inappropriate to correlate to the ability of RBCs to correctly circulate in the microvasculature.

Recently, experiments have shown that under moderate shear flows, RBCs display a large variety of regimes of motion among which typical tumbling, rolling and tank-treading motions (FIG. 1), and that the regime of motion observed at a given shear stress was governed by the cell deformability. Simultaneously, models and numerical simulations explained the role played by each mechanical parameter on the type of motion and on the shear-stress triggered transition between different motions. This approach allowed to highlight several new parameters such as the orbit of RBCs tumbling in the flow and the critical stress of motion transition, easily measurable and directly linked to RBC deformability. This approach, however, focused primarily on RBCs collected from healthy donors. So far, it has not been exploited to highlight modifications of RBC deformability due to diseases or to changes in physiology or environment.

The aim of the invention is to obviate these drawbacks.

One of the purposes of the invention is to provide a method using a marker sensitive to the RBCs deformability and easily measurable.

Another purpose of the invention is to provide a method for predicting the occurrence of a complication associated with the red blood cells deformability.

An additional purpose of the invention is to provide a method for tracking the red blood cell deformability with a marker.

Another purpose of the invention is to provide a device for carrying out the said three methods.

Thus, the invention relates to a method for the determination, preferably the in vitro determination, of the variation of the deformability of red blood cells of a tested individual, the method comprising the steps of:

a) determining a first amount of red blood cells having a tank-treading motion in a population of red blood cells, said population of red blood cells being obtained from a sample of said tested individual, b) calculating the absolute value of the difference between said first amount of red blood cells having a tank-treading motion in a population of red blood cells, and a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, wherein said reference populations are obtained either from at least two independent samples of said tested individual, or from at least one sample of at least two individuals, said at least two individuals being different from said tested individual, such that if said absolute value is greater or higher than twice the value of said standard deviation, then the red blood cells of said population present a significant variation of their deformability compared to the red blood cells of said reference populations.

The invention is based on the unexpected observation made by the inventors that an easily measurable parameter of motion, namely the proportion of tank-treading RBCs in a (large) RBCs collection, senses a combination of the mechanical parameters of the RBCs in the collection and is sensitive to the RBC density and inner water content. Therefore, the invention is useful for easily tracking the variability of red blood cells deformability of an individual for any disease or condition such as blood storage, gamma irradiation, artificial triac valves, intensive sports training, ageing, etc.

More precisely, the tank-treading motion of the red blood cells in a flow can be defined by a motion wherein the membrane of said red blood cells tank-treads, i.e. rotates around the centre of mass of the cell, and its orientation oscillates (swings) around a mean value.

In shear flow at low shear stresses (<1 Pa), the shape of healthy RBCs does not significantly deviate from the physiological biconcave shape. However, the local resistance to shear stress of the cell membrane and the viscous dissipation in the cytoplasm are responsible for a large variety of cell motion even in the low deformation regime.

Indeed, tumbling, flip-flopping, rolling, and tank-treading motions of healthy RBCs have been observed in shear flows upon increasing shear stress. More precisely, at very low shear stress (<0.04 Pa), a healthy RBC tumbles in the flow like a rigid body with its axis of symmetry lying, on average, in the shear plane. When the shear stress increases, the RBC progressively changes its orbit to display a complex flip-flopping motion with a precession motion of its axis of symmetry (FIG. 1A).

Upon further increase of the shear stress (0.07 to 0.15 Pa), the orbital angle rotates by 90° from the initial orbital angle of tumbling and RBCs reach a stable regime of rolling, in which the cell spins in the shear plane and rolls on its edge like a wheel (FIG. 1B). Below a critical value of the viscosity contrast, defined as the ratio of the cell effective viscosity (which combines membrane and cytoplasmic viscosities) to the viscosity of the suspending fluid, and upon further increase of the shear rate, healthy RBCs present a fluidized regime analogous to that of a droplet. The membrane tank-treads, i.e. rotates around the centre of mass of the cell, its axis of symmetry lies in the shear plane and its orientation oscillates (swings) around a mean value (FIG. 1C).

The principle of the method of the invention is to compare two amounts, namely the first amount and the second amount, which are respectively the result of a ratio of RBCs having a tank-treading motion in a population, and the mean value of ratios of RBCs having a tank-treading motion in reference populations. In other words, the first and second amounts represent the proportion of RBCs having a tank-treading motion among all the motions presented by the RBCs of the population, such as tumbling, rolling and tank-treading motions. Thus, these first and second amounts are both comprised between 0 and 1, with 0 corresponding to none of RBCs of the population(s) having a tank-treading motion, and 1 corresponding to all the RBCs of the population(s) having a tank-treading motion.

The comparison of the first and the second amounts is carried out by calculating the absolute value of the difference between said first and second amounts, and by comparing said absolute value to the value of the standard deviation (SD) of the red blood cells having a tank-treading motion obtained in the reference populations of red blood cells.

For considering that the red blood cells of the tested population present a significant variation of their deformability compared to the red blood cells of the reference populations, said absolute value has to be greater or higher than twice the value of said standard deviation.

The standard deviation (SD) is a measure that is used to quantify the amount of variation or dispersion of a set of data values. A low standard deviation indicates that the data points tend to be close to the mean (also called the expected value) of the set, while a high standard deviation indicates that the data points are spread out over a wider range of values.

The standard deviation can be calculated according to the following formula:

$$S = \sqrt{\frac{\sum_{i=1}^{N}(x_i - \bar{x})^2}{N-1}}$$

where $\{x_1, x_2, \ldots, x_N\}$ are the observed values of the sample items, x is the mean value of these observations, and N is the number of observations in the sample.

The value equal to "twice the value of the standard deviation" (2*SD) is commonly used in Statistics to challenge if a given number x is statistically significantly different or not to a mean value y. If the number x differs from y by less than 2*SD or if the difference is equal to 2*SD, it has to be considered that the number x is not statistically significantly different from y. Alternatively, if the number x differs from y by more than 2*SD, it has to be considered that the number x is statistically significantly different from y.

Accordingly, if the calculated absolute value is greater or higher than 2*SD, is has to be considered that the RBCs constituting the tested population present, on average, a variation of their deformability compared to that of the RBCs constituting the reference populations.

To determine if this variation corresponds to an increase or a decrease of the RBC deformability, it has to be considered in step b) the calculation of the value of the difference which is not the absolute value.

In such a case, the calculated value would either be a positive value or a negative value.

If the said calculated value is a positive value and is greater or higher than 2*SD, it has to be considered that the RBCs constituting the tested population present, on average, an increase of the deformability compared to the RBCs constituting the reference populations.

If the said calculated value is a negative value and less than −2*SD, it has to be considered that the RBCs constituting the tested population present, on average, a decrease of the deformability compared to the RBCs constituting the reference populations.

Furthermore, if the said calculated value is a positive value and less than 2*SD, or if the said calculated value is a negative value and greater or higher than −2*SD, or if the said calculated absolute value is less than 2*SD, it has to be considered that the RBCs constituting the tested population present, on average, the same deformability than the RBCs constituting the reference populations.

For establishing the first amount, a sample, more precisely a blood sample, of the tested individual is obtained by any conventional techniques known in the art, such as a needle or lancet, and a storage in a tank such as a tube, syringe, bottle or a flask. Said blood sample can be either a venous blood sample or an arterial blood sample.

The blood sample can be obtained either directly from said tested individual or indirectly from a blood bag containing a blood sample of the said tested individual.

The tested individual can be a human being or an animal as well.

For establishing the second amount, either at least two independent samples of said tested individual, or at least one sample of at least two individuals, said at least two individuals being different from said tested individual, are obtained.

In case of at least two independent samples of said tested individual, the blood samples can be obtained either directly from the said tested individual or indirectly from at least one blood bag containing a blood sample of the said tested individual.

In case of at least one sample of at least two individuals, said at least two individuals being different from said tested individual, the blood samples can be obtained either directly from the said individuals or indirectly from at least one blood bag containing a blood sample of each one of said individuals.

In either of the two cases mentioned above, the blood samples used for the reference populations are advantageously obtained in a period when said tested individual or said individuals are healthy, or free of any complication due to a condition or an inter-current event.

Advantageously, the blood samples used for the reference populations are obtained on the same day. Alternatively, the blood samples used for the reference populations are obtained on different days, advantageously at least one day apart, for example two days apart or three days apart.

In one embodiment, the tested individual is afflicted with a disease and the said individuals are also afflicted with the said disease.

In another embodiment, the tested individual is in a specific condition and the said individuals are in the same condition. For example, the said individuals are classified into the same age group than the said individual. Typically, the age groups can be classified as 0 to 26, 27 to 65 and more than 65 years old.

In one embodiment, said reference populations are obtained from at least three independent samples of said tested individual, more advantageously at least four blood samples, in particular at least five blood samples.

In one embodiment, said reference populations are obtained from at least one sample of at least 10 individuals, advantageously of at least 20 individuals, of at least 30 individuals, of at least 50 individuals, of at least 100 individuals or of at least 200 individuals.

In one embodiment, the first amount is the calculated mean of the determined amount of red blood cells having a tank-treading motion obtained in populations of red blood cells.

Advantageously, the invention also relates to a method for the determination, preferably the in vitro determination, of the variation of the deformability of red blood cells of a tested individual, the method comprising the steps of:

a) determining a first amount being the calculated mean of the determined amount of red blood cells having a tank-treading motion obtained in populations of red blood cells, said populations of red blood cells being obtained from at least two samples of said tested individual, b) calculating the absolute value of the difference between said first amount of red blood cells having a tank-treading motion in populations of red blood cells, and a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, wherein said reference populations are obtained either from at least two independent samples of said tested individual, or from at least one sample of at least two individuals, said at least two individuals being different from said tested individual, such that if said absolute value is greater or higher than twice the value of said standard deviation (SD), then the red blood cells of said population present a significant variation of their deformability compared to the red blood cells of said reference populations.

In such an embodiment and advantageously, the blood samples used for the populations are obtained the same day. Alternatively, the blood samples used for the populations are obtained on different days, advantageously at least one day apart, for example two days apart or three days apart.

Advantageously, said populations are obtained from at least three independent samples of said tested individual, more advantageously at least four blood samples, in particular at least five blood samples.

After obtaining said blood samples, the RBCs can be isolated from the other constituents of blood, for example by centrifugation, or the blood sample can be directly diluted, for example in a solution of Dextran.

Afterwards, the RBCs are subjected to a flow and tracked using visualisation means to determine the motion of each RBC, such as tumbling, rolling and tank-treading. The RBCs circulate in a circulation means/member which can be a flow chamber, advantageously a flow chamber with a cone-plan geometry or a microchannel, more advantageously an optically transparent and parallelepipedic flow chamber. The circulation member has a boundary wall that is perpendicular to the direction of the flow gradient. For example, the parallelepipedic flow chamber has two boundary walls.

The said flow is generated by a generate means such as a pump, a syringe pump, or a pressure controller.

Advantageously, the invention relates to the method as defined above, wherein for said determination of the first and second amounts, the red blood cell populations are subjected to a flow having a wall shear rate from $1\ s^{-1}$ to $50\ s^{-1}$, and a viscosity from $10^{-3}\ Pa\cdot s$ to $10^{-1}\ Pa\cdot s$. This flow conditions enable the occurrence of tank-treading motion of at least a part of the red blood cells in the red blood cells population.

By "from $1\ s^{-1}$ to $50\ s^{-1}$" it is meant in the invention $1\ s^{-1}$, $2\ s^{-1}$, $3\ s^{-1}$, $4\ s^{-1}$, $5\ s^{-1}$, $6\ s^{-1}$, $7\ s^{-1}$, $8\ s^{-1}$, $9\ s^{-1}$, $10\ s^{-1}$, $11\ s^{-1}$, $12\ s^{-1}$, $13\ s^{-1}$, $14\ s^{-1}$, $15\ s^{-1}$, $16\ s^{-1}$, $17\ s^{-1}$, $18\ s^{-1}$, $19\ s^{-1}$, $20\ s^{-1}$, $21\ s^{-1}$, $22\ s^{-1}$, $23\ s^{-1}$, $24\ s^{-1}$, $25\ s^{-1}$, $26\ s^{-1}$, $27\ s^{-1}$, $28\ s^{-1}$, $29\ s^{-1}$, $30\ s^{-1}$, $31\ s^{-1}$, $32\ s^{-1}$, $33\ s^{-1}$, $34\ s^{-1}$, $35\ s^{-1}$, $36\ s^{-1}$, $37\ s^{-1}$, $38\ s^{-1}$, $39\ s^{-1}$, $40\ s^{-1}$, $41\ s^{-1}$, $42\ s^{-1}$, $43\ s^{-1}$, $44\ s^{-1}$, $45\ s^{-1}$, $46\ s^{-1}$, $47\ s^{-1}$, $48\ s^{-1}$, $49\ s^{-1}$, $50\ s^{-1}$.

By "from $10^{-3}\ Pa\cdot s$ to $10^{-1}\ Pa\cdot s$" it is meant in the invention $0.01*10^{-1}\ Pa\cdot s$, $0.02*10^{-1}\ Pa\cdot s$, $0.03*10^{-1}\ Pa\cdot s$, $0.04*10^{-1}\ Pa\cdot s$, $0.05*10^{-1}\ Pa\cdot s$, $0.06*10^{-1}\ Pa\cdot s$, $0.07*10^{-1}\ Pa\cdot s$, $0.08*10^{-1}\ Pa\cdot s$, $0.09*10^{-1}\ Pa\cdot s$, $0.1*10^{-1}\ Pa\cdot s$, $0.11*10^{-1}\ Pa\cdot s$, $0.12*10^{-1}\ Pa\cdot s$, $0.13*10^{-1}\ Pa\cdot s$, $0.14*10^{-1}\ Pa\cdot s$, $0.15*10^{-1}\ Pa\cdot s$, $0.16*10^{-1}\ Pa\cdot s$, $0.17*10^{-1}\ Pa\cdot s$, $0.18*10^{-1}\ Pa\cdot s$, $0.19*10^{-1}\ Pa\cdot s$, $0.2*10^{-1}\ Pa\cdot s$, $0.21*10^{-1}\ Pa\cdot s$, $0.22*10^{-1}\ Pa\cdot s$, $0.23*10^{-1}\ Pa\cdot s$, $0.24*10^{-1}\ Pa\cdot s$, $0.25*10^{-1}\ Pa\cdot s$, $0.26*10^{-1}\ Pa\cdot s$, $0.27*10^{-1}\ Pa\cdot s$, $0.28*10^{-1}\ Pa\cdot s$, $0.29*10^{-1}\ Pa\cdot s$, $0.3*10^{-1}\ Pa\cdot s$, $0.31*10^{-1}\ Pa\cdot s$, $0.32*10^{-1}\ Pa\cdot s$, $0.33*10^{-1}\ Pa\cdot s$, $0.34*10^{-1}\ Pa\cdot s$, $0.35*10^{-1}\ Pa\cdot s$, $0.36*10^{-1}\ Pa\cdot s$, $0.37*10^{-1}\ Pa\cdot s$, $0.38*10^{-1}\ Pa\cdot s$, $0.39*10^{-1}\ Pa\cdot s$, $0.4*10^{-1}\ Pa\cdot s$, $0.41*10^{-1}\ Pa\cdot s$, $0.42*10^{-1}\ Pa\cdot s$, $0.43*10^{-1}\ Pa\cdot s$, $0.44*10^{-1}\ Pa\cdot s$, $0.45*10^{-1}\ Pa\cdot s$, $0.46*10^{-1}\ Pa\cdot s$, $0.47*10^{-1}\ Pa\cdot s$, $0.48*10^{-1}\ Pa\cdot s$, $0.49*10^{-1}\ Pa\cdot s$, $0.5*10^{-1}\ Pa\cdot s$, $0.51*10^{-1}\ Pa\cdot s$, $0.52*10^{-1}\ Pa\cdot s$, $0.53*10^{-1}\ Pa\cdot s$, $0.54*10^{-1}\ Pa\cdot s$, $0.55*10^{-1}\ Pa\cdot s$, $0.56*10^{-1}\ Pa\cdot s$, $0.57*10^{-1}\ Pa\cdot s$, $0.58*10^{-1}\ Pa\cdot s$, $0.59*10^{-1}\ Pa\cdot s$, $0.6*10^{-1}\ Pa\cdot s$, $0.61*10^{-1}\ Pa\cdot s$, $0.62*10^{-1}\ Pa\cdot s$, $0.63*10^{-1}\ Pa\cdot s$, $0.64*10^{-1}\ Pa\cdot s$, $0.65*10^{-1}\ Pa\cdot s$, $0.66*10^{-1}\ Pa\cdot s$, $0.67*10^{-1}\ Pa\cdot s$, $0.68*10^{-1}\ Pa\cdot s$, $0.69*10^{-1}\ Pa\cdot s$, $0.7*10^{-1}\ Pa\cdot s$, $0.71*10^{-1}\ Pa\cdot s$, $0.72*10^{-1}\ Pa\cdot s$, $0.73*10^{-1}\ Pa\cdot s$, $0.74*10^{-1}\ Pa\cdot s$, $0.75*10^{-1}\ Pa\cdot s$, $0.76*10^{-1}\ Pa\cdot s$, $0.77*10^{-1}\ Pa\cdot s$, $0.78*10^{-1}\ Pa\cdot s$, $0.79*10^{-1}\ Pa\cdot s$, $0.8*10^{-1}\ Pa\cdot s$, $0.81*10^{-1}\ Pa\cdot s$, $0.82*10^{-1}\ Pa\cdot s$, $0.83*10^{-1}\ Pa\cdot s$, $0.84*10^{-1}\ Pa\cdot s$, $0.85*10^{-1}\ Pa\cdot s$, $0.86*10^{-1}\ Pa\cdot s$, $0.87*10^{-1}\ Pa\cdot s$, $0.88*10^{-1}\ Pa\cdot s$, $0.89*10^{-1}\ Pa\cdot s$, $0.9*10^{-1}\ Pa\cdot s$, $0.91*10^{-1}\ Pa\cdot s$, $0.92*10^{-1}\ Pa\cdot s$, $0.93*10^{-1}\ Pa\cdot s$, $0.94*10^{-1}\ Pa\cdot s$, $0.95*10^{-1}\ Pa\cdot s$, $0.96*10^{-1}\ Pa\cdot s$, $0.97*10^{-1}\ Pa\cdot s$, $0.98*10^{-1}\ Pa\cdot s$, $0.99*10^{-1}\ Pa\cdot s$, $1*10^{-1}\ Pa\cdot s$.

These flow conditions are advantageous for highlighting the variability of the amount of tank-treading RBCs of different red blood cell populations presenting different deformability properties when using a visualisation means for determining the type of motion of said RBCs.

During the tracking, said RBCs are observed and counted by a visualisation means/member such as brightfield microscopy, by using an inverted microscope or optical lenses. The visualisation member comprises an objective through which the light enters. The determination of the type of motion of each red blood cell in the shear flow can be done directly with the eyes or carried out by an image processing technique or a computer program, as detailed below.

In particular, the red blood cells of the population can be observed in brightfield microscopy along the direction of the flow gradient, by focusing at a chosen distance h from the boundary wall of the circulation member where the flow has constant shear rate. Method for determining regions of the flow with constant shear rate are well known in the art. For example, focusing at the distance h using an inverted microscope may be achieved by tuning the objective position, which is well controlled in an inverted microscope. In case the circulation member is a parallelepipedic flow chamber or a microchannel, the distance h may be fixed at a value of at most 40% of the distance of the circulation member from the boundary wall, to ensure that the shear rate is constant. Indeed, the shear rate of the flow at a distance above 40% of the distance h shows inconsistent shear rate. By "at most 40%", it is meant in the invention 40%, 39.5%, 39%, 38.5%, 38%, 37.5%, 37%, 36.5%, 36%, 35.5%, 35%, 34.5%, 34%, 33.5%, 33%, 32.5%, 32%, 31.5%, 31%, 30.5%, 30%, 29.5%, 29%, 28.5%, 28%, 27.5%, 27%, 26.5%, 26%, 25.5%, 25%, 24.5%, 24%, 23.5%, 23%, 22.5%, 22%, 21.5%, 21%, 20.5%, 20%, 19.5%, 19%, 18.5%, 18%, 17.5%, 17%, 16.5%, 16%, 15.5%, 15%, 14.5%, 14%, 13.5%, 13%, 12.5%, 12%, 11.5%, 11%, 10.5%, 10%, 9.5%, 9%, 8.5%, 8%, 7.5%, 7%, 6.5%, 6%, 5.5%, 5%, 4.5%, 4%, 3.5%, 3%, 2.5%, 2%, 1.5%, 1% and 0.5%. Notably, in case the circulation means has a height of 1 mm, the distance h may be 100 µm.

Only RBCs flowing in a localized layer centred at the chosen distance h and of thickness equal to the depth of field of the objective of the visualisation member plus or minus 2 µm are sharp in the observation field, and thereby in the recorded images of their movement, as described below. At least a part of the RBCs circulating in this localized layer are kept for analysis.

The flow of RBCs may be focused in this localized layer, for example by means of a co-flow of at least two fluids, only one of the fluids containing the RBCs. Apart from the RBCs, the at least two fluids may have the same composition or different compositions. The flow rate of each fluid can be different. Advantageously, the fluids have close refractive indices. As an example, one fluid may be dextrose 10% and the other fluid may be a 10% sucrose solution.

The flow of RBCs may also be focused in an extended layer centred at the distance h and of thickness corresponding to at most 2, 3, 4 or 5 times the depth of field of the objective of the visualisation member, by means of a co-flow of two fluids as described above. The RBCs flowing outside the depth of field are slightly blurred but their movement can be determined by steps of a computer program as described below.

Alternatively, the RBCs may flow at the whole height of the circulating member in the flow medium. When RBCs flow outside the extended layer, they are too blurred for determining their movement and may be eliminated during image processing and analysis by a computer program. In that particular case, the method can comprise sub-steps for excluding the blurred RBCs as detailed below.

In an embodiment, the visualisation means/member is associated with a video recorder for recording the motion of the red blood cells. According to this embodiment, it is possible to analyse the images of the recorded video away from the place where the images are acquired. More details about such embodiment are provided below.

More precisely, at least one video of moving red blood cells passing from one side to the other of the observation field (L denotes the length of the observation field along the direction of the flow) of a visualisation member, like a camera, can be recorded with a video recorder that records the projected shapes of the cells in a plane perpendicular to the direction of the flow gradient (orthogonal projection). The video recorder can be integrated into the visualization member. Images can be in greyscale.

The minimum length of the observation field L and the minimum observation time T of the video or each video can be determined to allow observation of at least half a period of the tumbling/flip-flopping motion of RBCs in the field of view of the visualisation member. This means that, for a tumbling/flip-flopping RBC of regular discoid shape, the axis of symmetry (axis of revolution of the discoid shape) lies at least one time in a plane perpendicular to the direction of the flow gradient, when the RBC is viewed on its edge. In the case of the parallelepipedic flow chamber, the relationship between the shear rate ($\dot{\gamma}$), h, L et T are well known in the art for a tumbling/flip-flopping RBC and reported in the document "Full dynamics of a red blood cell in shear flow, Jules Dupire, Marius Socol, and Annie Viallat, PNAS, 2012, doi/10.1073/pnas.1210236109", which is integrated in its entirety. L and T are given by the following equations:

$$T = 3\frac{\pi}{\dot{\gamma}} \text{ and } L = 3\pi h.$$

Each video consists of at least 5 images successively recorded using the video recorder. In each image RBCs can be individually isolated. Then, each RBC is tracked from one image to the next one in order to determine its movement in the observation field. The temporal evolution of the projected shape of a particular RBC in the successive images allows to identify its motion. To this purpose, standard techniques of image processing and analysis may be used.

First, from the video or each video, a motion sequence for each moving object can be obtained by extracting from each successive image a part of the image, corresponding to an individual image, showing only the projected shape of one and the same moving object, especially of one of the red blood cells. The succession of individual images shows the displacement of the object from one side of the observation field to the other side.

The said individual image can be obtained by a tracking method using a bounding box fitted around the projected shape of the said moving object. The different individual images for a particular moving object form the motion sequence.

The motion sequence of a particular moving object may be obtained by performing a tracking method comprising the following steps:
1) removing background in each image of the video or, in case of a plurality of videos, of the video containing the particular object, through median averaging in time,
2) detecting moving objects by threshold the standard deviation of pixels,
3) cross-correlating objects to sequential frames,
4) linking objects into tracks,
5) extracting the track images by extracting a square image around the detected objects in the video images (images from which the background has been removed) to obtain the corresponding motion sequence.

Steps 1) to 5) may be performed using MATLAB® software.

In particular, step 1) may comprise a first sub-step of importing in a computer program configured for image processing, such as MATLAB®, the greyscale images of the original video, corresponding to the video or, in case of a plurality of videos, to the one containing the particular object, as a three-dimensional tensor of unsigned 8-bit integers (uint8), the third dimension representing time. In a second sub-step of step 1), at least the first 10 images may be selected from the original video. In particular, at least the first 100 images may be selected in case the video has 25 images per second. The median image is then determined, wherein the median image corresponds to an image for which each pixel is the median of the values of that same pixel for all the selected images. This median image represents the background, showing the image of the chamber without any moving objects, since the contribution of moving objects is canceled out by the median averaging. In a third sub-step, the original video (the 3D uint8 tensor) is converted to 32 bit float numbers. For each image of the original video, the difference between the image and the median image is calculated and replaces the said image by the resulting image. The minimal and maximum values of the entire tensor are used to rescale the pixels values to numbers in the 0-255 range. Pixels values are then rounded and converted back to unsigned 8-bit integers.

Step 2) may comprise a sequential process of each image of original video to detect every moving object in the frame and extract features corresponding to these objects. This sequential process may be performed for each image by the following sub-steps:

converting the original video to 32-bit float numbers, applying a 2-D adaptive noise-removal filter. In case of using MATLAB® software, this step may be performed by wiener2 function of the image processing toolbox with a 3×3 pixels kernel, applying a standard deviation filter to highlight objects which contrast starkly against the background values and obtaining a resulting image. In case of using MATLAB® software, this step may be performed by stdfilt function of the image processing toolbox with a 5×5 pixels kernel, binarizing the resulting image, in particular using a threshold of 2, and obtaining a binary image showing all pixels whose standard deviation compared to the surrounding area, in particular 5×5 pixels, is superior to the threshold.

performing morphological operations on the binary image to complete the outlines of the objects and to fill the holes. In case of using MATLAB® software, this step may be performed by imclose function with a kernel of 5×5 pixels followed by the imfill functions to fill holes, identifying objects. In case of using MATLAB® software, this step may be performed by regionprops function. For each object, the following features are extracted:

the area (number of non-zero pixels of the image)

the bounding box (the coordinates of the smallest rectangle containing the object)

the center of mass of the object (X and Y position within the image)

pixel index list (full list of the pixels containing the object, identified as a subset of the pixels of the full image)

the individual image of the object (portion of the original image corresponding to the bounding box of the object)

all features of all objects are stored within a data structure.

For each image of the original video, a data structure containing all the objects and corresponding features is obtained. All these data structures are collected for every image and stored in a super-structure for the whole video or the whole original video.

Step 3) may comprise for each object obtained in step 2), the calculation of the likely position of the object in a sequential image (previous or next image) by cross-correlating the image of the object in a current image with the sequential image. Then, a normalized cross-correlation may be calculated, in particular using the normxcorr2 function of MATLAB® software. The image of the object is cross-correlated with a strip, which may be extracted from the sequential image. This strip has the full width of the image, but is limited in height to be of the same height as the individual image of the object and contains the region where the object is located in current whole image. Then the maximum correlation value may be looked for in the direction the object is expected to be (left for the previous image, or right for the next, with no Y-movement). For each object, the XY position may be extracted of the likely position of the object in the previous image and the likely position in the next image. The value of the normalized correlation may also be extracted at the found maxima.

Step 4) may comprise the identification of the objects belonging to a same track through the overlap between their expected positions in sequential frames and their positions in their respective frames. Objects are considered as overlapping if the expected position is contained within the bounding box of the sequential. Measures may be taken to identify special cases:

Objects with no previous frame objects appearing from the left of the image (this marks the beginning of a new track);

Objects with no next frame objects disappearing through the right of the image (this marks the end of the track);

Objects with two or more previous image objects (merging tracks). Tracks which are merged are tagged as such from the relevant images;

Objects with two or more next image objects (splitting tracks). The merged part of the tracks is duplicated in all split tracks;

Objects with no previous images or no next image objects which are not near the relevant image border (objects whose sequential objects have not been detected through the object detection algorithm). These objects and relevant tracks are excluded from next steps.

Each track is formed by the sequence of objects in sequential images. All features of the objects as well as the image numbers to which the objects belong may be stored within a track structure.

Step 5) may comprise, for each image of the track of the particular object, the extraction of a normalized image from the original video images. Using the XY-coordinates of the object and the image number, a normalized square image is extracted from the video image centered on the object position.

The projected shape of an object in each individual image can be fitted with an ellipse, in particular by means of conventional methods known in the art. Notably, the ellipse can be obtained in step 2) of the aforementioned tracking method when extracting features of each object, especially by using fitellipse function in MATLAB® or by using macros/functions developed for ImageJ® such as DrawEllipse, EllipseFitter or directly by using Analyze Particles function of ImageJ applied to the image of the object.

ImageJ® is a Java-based image processing program developed at the National Institutes of Health.

Said ellipse helps to determine the major and the minor axis of the shape of said object in each individual image. Afterwards, major and minor axis of the ellipse will be considered as corresponding to the major and minor axis of the respective projected shape.

In case of greyscale images, the projected shape of an object in each individual image of one of the motion sequences may be determined by the grey level intensity gradients of the image pixels between the background pixels (medium and uniform grey level intensity) and the pixels corresponding to the object (low or high grey level intensities). Each projected shape is then associated with a grey level intensity profile.

The motion of impurities like debris and dust can be recorded and must be excluded from the analysis in order to correctly determine the proportion of red blood cell in tank treading motion in the population. To that purpose, a motion sequence where the major axis of the ellipse observed on each individual image is smaller than 6 µm is excluded from the analysis. Such object is not an RBC but an impurity (debris, dust). Thereafter, the remaining motion sequences correspond solely to RBC motions.

In case part of the red blood cells circulate outside the extended layer, the method can include a step of excluding the RBCs which are too blurred from the analysis. In the case of the parallelepipedic flow chamber, excluding can be done by carrying out the following sub-steps:

counting the number of individual images constituting the motion sequence of each red blood cell crossing the observation field, excluding the red blood cells whose motion sequence has a number of individual images larger or smaller than $N \pm 1$, where N is equal to the value of the frame rate of the recording member multiplied by the length along the flow direction of the observation field divided by the product of the shear rate to the distance h.

N is here the number of images in the motion sequence expected for an RBC circulating at the distance h from the boundary wall of the parallelepipedic flow chamber.

Based on the remaining motion sequences, the red blood cells are classified as having a tank-treading motion or another motion. The other motion category includes rolling, tumbling and flip-flopping motions.

To be considered as pertaining to the other motion category, the motion sequence of a said red blood cell has to comprise at least two images for which the ratio between the minor axis and the major axis of the projected shape is less than 0.45. These at least two images correspond to a red blood cell viewed almost on its edge.

To be considered as pertaining to the tank treading motion category, all the individual images of the motion sequence of a red blood cell show a projected shape with a ratio between the minor axis and the major axis greater than 0.45. Indeed, in the observation conditions set above, a red blood cell in tank treading motion cannot be viewed on its edge. This can be explained by the fact that when an RBC tank-treads, its axis of symmetry remains (or oscillates weakly) along the direction of the flow gradient, and the projection of the RBC's shape onto the observation plane is then quasi-circular with a biconcave portion in the centre. To confirm the existence of a biconcave portion in the centre of the projected shape through the motion sequence, the grey level intensity profile of each ellipse of a particular red blood cell along any segment passing through the centre of the ellipse and bounded by the contour of the ellipse is analysed. This biconcavity (non-constant cell thickness) results in a grey-level intensity difference between the periphery and the centre of the cell (dimple). Therefore, if the grey level intensity profile of 90% of the ellipses in the sequence of a particular red blood cell has two extrema separated by at least 1 µm, the red blood cell is considered to maintain a stable orientation and therefore tank-treads. Accordingly, the red blood cell is classified in the tank treading motion category. In case this criterium is not respected, the red blood cell is not considered as pertaining to the tank treading category and it is no longer considered for the analysis.

The different steps for determining the first amount, from the subjecting to the flow step to the classification step, can be computer implemented and performed automatically by a control module.

The invention also relates to a method for the prediction, preferably the in vitro prediction, of a vaso-occlusive crisis of a tested individual afflicted with a sickle-cell disease, the method comprising the steps of:

a) determining a first amount of red blood cells having a tank-treading motion in a population of red blood cells, said population of red blood cells being obtained from a sample of said tested individual, b) calculating the value of the difference between a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, and the said first amount of red blood cells having a tank-treading motion in a population of red blood cells, wherein said reference populations are obtained from at least two independent samples of said tested individual, in a period outside an episode of a vaso-occlusive crisis, such that if said value of the difference is a positive value greater or higher than twice the value of said standard deviation, then said tested individual is predicted to be susceptible to experience, within 72 hours, a vaso-occlusive crisis, i.e. said tested patient is liable to experience within 72 hours, a vaso-occlusive crisis.

With more than 50 million individuals afflicted worldwide, sickle-cell disease (SCD), is the most common genetic disease. Sickle-cell disease is an inherited blood disorder caused by sickle haemoglobin (HbS), a variant of the haemoglobin (Hb) molecule. Upon deoxygenation, HbS polymerizes and self-assembles into fibres in the cytoplasm, resulting in sickled-shaped cells. SCD is responsible for unpredictable painful vaso-occlusive crises that can be life-threatening. In both oxygenated and deoxygenated cases, the mechanical properties of SCD RBCs are altered in comparison to healthy ones.

This disease leads to the occurrence of vaso-occlusive crises which are painful complications. These crises are caused by blood vessels circulation problems, when the circulation in blood vessels is obstructed by sickle-shaped red blood cells, causing ischemic injuries. The most common complaint is of pain, and recurrent episodes can cause irreversible organ damage. One of the most severe forms is acute chest syndrome, which occurs following a pulmonary parenchyma infarction. This can quickly lead to death. Other types of vaso-occlusive crises in sickle cell disease include dactylitis, priapism, abdominal pain, and jaundice.

When the patient suffers from too frequent crises, preventive treatments exist and consist mainly of transfusion exchange and induction of foetal haemoglobin.

In the other cases or when preventive treatments are not efficient, patients are not treated with such preventive treatments. Unfortunately, there is no method for predicting the occurrence of said vaso-occlusive crisis, and said patients are condemned to wait for the next crisis before being hospitalized.

Consequently, there was a need for a method of predicting the imminence of such a crisis.

The inventors unexpectedly observed that the proportion of tank-treading RBCs is a relevant marker for the occurrence of a vaso-occlusive crisis of patients afflicted with sickle cell disease. The inventors showed that the proportion of tank-treading RBCs decreases in a significant way before the vaso-occlusive crisis occurs so that it is possible to predict the occurrence of a vaso-occlusive crisis. Consequently, the patients can be treated with a preventive treatment at home or in the hospital, before the crisis occurs.

Furthermore, this method of prediction may allow obtaining the prognosis of a patient afflicted with SCD regarding the experience of a vaso-occlusive crisis. Such a prognosis is a "short-term" prognosis since it can determine within about 72 hours if the patient will experience a vaso-occlusive crisis.

Here again, the principle of the method of the invention is to compare two amounts, namely the first and second amounts, which are respectively the result of a ratio of RBCs having a tank-treading motion in a population, and the mean value of ratios of RBCs having a tank-treading motion in reference populations.

Thus, these first and second amounts are both comprised between 0 and 1, with 0 corresponding to none of the red blood cells of the population(s) having a tank-treading motion, and 1 corresponding to all red blood cells of the population(s) having a tank-treading motion.

In such an embodiment, the comparison of the first and second amounts is carried out by calculating the value of the difference between the second and the first amounts, and by comparing said calculated value to the value of the standard deviation of the red blood cells having a tank-treading motion obtained in the reference populations of red blood cells. Accordingly, the calculation has to be carried out in the established order.

In such an embodiment, step b) relates to the following formula:

$$x = v_{control} - v_{sample}$$

wherein, x corresponds to the calculated value;

$v_{control}$ corresponds to the value of the second amount; and $v_{sample}$ corresponds to the value of the first amount.

To consider that the tested individual is predicted to be susceptible to experience, i.e. is liable to experience, a vaso-occlusive crisis within 72 hours, the said calculated value has to be greater or higher than twice the value of said standard deviation.

To be more accurate, if the calculated value is a positive value and is greater or higher than twice the value of said standard deviation, then the tested individual is prognosticated to be susceptible to experience a vaso-occlusive crisis within 72 hours.

If the said calculated value is less (including negative values) than twice the value of said standard deviation, it has to be considered that the tested individual is predicted as not likely to experience, i.e. is not liable to experience, a vaso-occlusive crisis within 72 hours.

The at least two independent samples of said tested individual for said reference populations are obtained outside a period of a vaso-occlusive crisis.

Advantageously, the invention relates to the method as defined above, in which the onset of a vaso-occlusive crisis is defined by the appearance of at least one first symptom selected from the group consisting of the appearance of a new bone pain affecting at least two territories, dyspnea or shortness of breath, and sputum.

Accordingly, the at least two independent samples of said tested individual for said reference populations are recovered in a period where the patient is not undergoing a vaso-occlusive crisis nor the above-mentioned first symptoms, which is qualified by an "out of crisis" period.

More advantageously, the at least two independent samples of said tested individual for said reference populations are obtained in a period after or before a vaso-occlusive crisis. Advantageously, the said reference populations are obtained at least 48 hours after a vaso-occlusive crisis. Alternatively, the said reference populations are obtained at least 96 hours before a vaso-occlusive crisis.

To establish the first and second amounts, a blood sample or blood samples of the tested individual are obtained by any conventional techniques known in the art, such as a needle or lancet, and a storage in a tank such as a tube, syringe, bottle or a flask.

The blood samples can be obtained either directly from said tested individual or indirectly from a blood bag containing a blood sample of the said tested individual.

Advantageously, at least three independent samples of said tested individual are used for said reference populations, more advantageously at least four blood samples, in particular at least five blood samples.

Advantageously, the blood samples used for the reference populations are obtained on the same day. Alternatively, the blood samples used for the reference populations are obtained on different days, advantageously at least one day apart, for example two days apart or three days apart.

In one embodiment, the first amount is the calculated mean of the determined amount of red blood cells having a tank-treading motion obtained in populations of red blood cells.

Advantageously, the invention also relates to a method for the prediction, advantageously the in vitro, prediction of a vaso-occlusive crisis of a tested individual afflicted with a sickle-cell disease, the method comprising the steps of:

a) determining a first amount being the calculated mean of the determined amount of red blood cells having a tank-treading motion obtained in populations of red blood cells, said populations of red blood cells being obtained from at least two samples of said tested individual, b) calculating the absolute value of the difference between
a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, and
said first amount of red blood cells having a tank-treading motion in populations of red blood cells,

US 12,656,334 B2

15 wherein said reference populations are obtained from at least two independent samples of said tested individual in a period outside an episode of a vaso-occlusive crisis, such that if said value of the difference is a positive value greater or higher than 2 fold the value of said standard deviation, then said tested individual is prognosticated to be susceptible to experience a vaso-occlusive crisis within 72 hours.

After the said blood samples are obtained, the RBCs can be isolated from the others constituents of the blood, for example by centrifugation, or the blood sample can be directly diluted, for example in solution of Dextran.

Afterwards, the RBCs are subjected to a shear flow and tracked using a visualisation means for determining the motion status of each RBC, such as tank-treading or other motion. The RBCs flow in a circulation means which can be a flow chamber, advantageously a microchannel, more advantageously a quartz flow chamber.

The said flow is generated by a generate means such as a pump or a syringe pump or a flow controller.

Advantageously, the invention relates to the method as defined above, wherein for said determination of the first and second amounts, the red blood cells populations are subjected to a flow having a wall shear rate from $1\ s^{-1}$ to $25\ s^{-1}$, and a viscosity from $10^{-3}$ Pa·s to $10^{-1}$ Pa·s.

By "$1\ s^{-1}$ to $25\ s^{-1}$" it is meant in the invention $1\ s^{-1}$, $2\ s^{-1}$, $3\ s^{-1}$, $4\ s^{-1}$, $5\ s^{-1}$, $6\ s^{-1}$, $7\ s^{-1}$, $8\ s^{-1}$, $9\ s^{-1}$, $10\ s^{-1}$, $11\ s^{-1}$, $12\ s^{-1}$, $13\ s^{-1}$, $14\ s^{-1}$, $15\ s^{-1}$, $16\ s^{-1}$, $17\ s^{-1}$, $18\ s^{-1}$, $19\ s^{-1}$, $20\ s^{-1}$, $21\ s^{-1}$, $22\ s^{-1}$, $23\ s^{-1}$, $24\ s^{-1}$, $25\ s^{-1}$.

By "from $10^{-3}$ Pa·s to $10^{-1}$ Pa·s" it is meant in the invention $0.01*10^{-1}$ Pa·s, $0.02*10^{-1}$ Pa·s, $0.03*10^{-1}$ Pa·s, $0.04*10^{-1}$ Pa·s, $0.05*10^{-1}$ Pa·s, $0.06*10^{-1}$ Pa·s, $0.07*10^{-1}$ Pa·s, $0.08*10^{-1}$ Pa·s, $0.09*10^{-1}$ Pa·s, $0.1*10^{-1}$ Pa·s, $0.11*10^{-1}$ Pa·s, $0.12*10^{-1}$ Pa·s, $0.13*10^{-1}$ Pa·s, $0.14*10^{-1}$ Pa·s, $0.15*10^{-1}$ Pa·s, $0.16*10^{-1}$ Pa·s, $0.17*10^{-1}$ Pa·s, $0.18*10^{-1}$ Pa·s, $0.19*10^{-1}$ Pa·s, $0.2*10^{-1}$ Pa·s, $0.21*10^{-1}$ Pa·s, $0.22*10^{-1}$ Pa·s, $0.23*10^{-1}$ Pa·s, $0.24*10^{-1}$ Pa·s, $0.25*10^{-1}$ Pa·s, $0.26*10^{-1}$ Pa·s, $0.27*10^{-1}$ Pa·s, $0.28*10^{-1}$ Pa·s, $0.29*10^{-1}$ Pa·s, $0.3*10^{-1}$ Pa·s, $0.31*10^{-1}$ Pa·s, $0.32*10^{-1}$ Pa·s, $0.33*10^{-1}$ Pa·s, $0.34*10^{-1}$ Pa·s, $0.35*10^{-1}$ Pa·s, $0.36*10^{-1}$ Pa·s, $0.37*10^{-1}$ Pa·s, $0.38*10^{-1}$ Pa·s, $0.39*10^{-1}$ Pa·s, $0.4*10^{-1}$ Pa·s, $0.41*10^{-1}$ Pa·s, $0.42*10^{-1}$ Pa·s, $0.43*10^{-1}$ Pa·s, $0.44*10^{-1}$ Pa·s, $0.45*10^{-1}$ Pa·s, $0.46*10^{-1}$ Pa·s, $0.47*10^{-1}$ Pa·s, $0.48*10^{-1}$ Pa·s, $0.49*10^{-1}$ Pa·s, $0.5*10^{-1}$ Pa·s, $0.51*10^{-1}$ Pa·s, $0.52*10^{-1}$ Pa·s, $0.53*10^{-1}$ Pa·s, $0.54*10^{-1}$ Pa·s, $0.55*10^{-1}$ Pa·s, $0.56*10^{-1}$ Pa·s, $0.57*10^{-1}$ Pa·s, $0.58*10^{-1}$ Pa·s, $0.59*10^{-1}$ Pa·s, $0.6*10^{-1}$ Pa·s, $0.61*10^{-1}$ Pa·s, $0.62*10^{-1}$ Pa·s, $0.63*10^{-1}$ Pa·s, $0.64*10^{-1}$ Pa·s, $0.65*10^{-1}$ Pa·s, $0.66*10^{-1}$ Pa·s, $0.67*10^{-1}$ Pa·s, $0.68*10^{-1}$ Pa·s, $0.69*10^{-1}$ Pa·s, $0.7*10^{-1}$ Pa·s, $0.71*10^{-1}$ Pa·s, $0.72*10^{-1}$ Pa·s, $0.73*10^{-1}$ Pa·s, $0.74*10^{-1}$ Pa·s, $0.75*10^{-1}$ Pa·s, $0.76*10^{-1}$ Pa·s, $0.77*10^{-1}$ Pa·s, $0.78*10^{-1}$ Pa·s, $0.79*10^{-1}$ Pa·s, $0.8*10^{-1}$ Pa·s, $0.81*10^{-1}$ Pa·s, $0.82*10^{-1}$ Pa·s, $0.83*10^{-1}$ Pa·s, $0.84*10^{-1}$ Pa·s, $0.85*10^{-1}$ Pa·s, $0.86*10^{-1}$ Pa·s, $0.87*10^{-1}$ Pa·s, $0.88*10^{-1}$ Pa·s, $0.89*10^{-1}$ Pa·s, $0.9*10^{-1}$ Pa·s, $0.91*10^{-1}$ Pa·s, $0.92*10^{-1}$ Pa·s, $0.93*10^{-1}$ Pa·s, $0.94*10^{-1}$ Pa·s, $0.95*10^{-1}$ Pa·s, $0.96*10^{-1}$ Pa·s, $0.97*10^{-1}$ Pa·s, $0.98*10^{-1}$ Pa·s, $0.99*10^{-1}$ Pa·s, $1*10^{-1}$ Pa·s.

Advantageously, the invention relates to the method as defined above, wherein said defined flow has a wall shear rate from $10\ s^{-1}$ to $20\ s^{-1}$. Advantageously, the invention relates to the method as defined above, wherein said defined flow has a viscosity from $3*10^{-2}$ Pa·s to $4.5*10^{-2}$ Pa·s.

These flow conditions are advantageous for highlighting the variability of the amount of tank-treading RBCs of different red blood cell populations presenting different deformability properties when using a visualisation means for determining the type of motion of said RBCs for individual afflicted with cell sickle disease.

During tracking, said RBCs are observed and counted by a visualisation means such as brightfield microscopy, inverted microscopy. The determination of the type of motion of each red blood cell in the shear flow can be done directly with the eyes or carried out by image processing, a computer program, as detailed further.

In an embodiment, the visualisation means are associated with a video recorder for recording the motion of the red blood cells. This embodiment allows analysing the images away from the place the images are taken. More detail about such embodiment is provided below.

The invention also relates to a method for the diagnosis of, advantageously the in vitro diagnosis of, i.e. for quantitatively evaluating, the response to a therapeutic treatment of a tested individual afflicted with a blood disorder affecting the deformability of the red blood cells and treated with said therapeutic treatment, said therapeutic treatment being directed to said blood disorder, method comprising the steps of:

a) determining a first amount of red blood cells having a tank-treading motion in a population of red blood cells, said population of red blood cells being obtained from a sample of said tested individual, b) calculating the value of the difference between said first amount of red blood cells having a tank-treading motion in a population of red blood cells, and a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, wherein said reference populations are obtained from at least two independent samples of said tested individual, before the beginning of said therapeutic treatment, such that if said value of the difference is greater or higher than twice the value of said standard deviation, said tested individual is considered to be responsive to the said therapeutic treatment.

This aspect of the invention comes from the unexpected observation made by the inventors that the clinical status of individuals afflicted with a blood disorder affecting the deformability of the red blood cells can be easily and inexpensively monitored by tracking the proportion of tank-treading RBCs in a red blood cells population.

To date, it is relevant to have a means for evaluating the efficiency of a treatment directed against blood disorders. The invention identifies that the proportion of tank-treading red blood cells in a population of red blood cells can help to evaluate this efficiency.

Here again, the principle of the method of the invention is to compare two amounts, namely the first and second amounts, which are respectively the result of a ratio of RBCs having a tank-treading motion in a population, and the mean value of ratios of RBCs having a tank-treading motion in reference populations.

Thus, these first and second amounts are both comprised between 0 and 1, with 0 corresponding to none of the red blood cells of the population(s) having a tank-treading motion, and 1 corresponding to all red blood cells of the population(s) having a tank-treading motion.

In such an embodiment, the comparison of the first and second amounts is carried out by calculating the value of the difference between the first and the second amount, and by comparing said calculated value to the value of the standard deviation of the red blood cells having a tank-treading motion obtained in the reference populations of red blood cells. Accordingly, the calculation has to be carried out in the established order.

In such an embodiment, step b) relates to the following formula:

$$x = v_{sample} - v_{control}$$

wherein, x corresponds to the calculated value;

$v_{control}$ corresponds to the value of the second amount; and $v_{sample}$ corresponds to the value of the first amount.

If the calculated value is a positive value and is greater or higher than twice the value of said standard deviation, then, said tested individual is considered responsive to the said therapeutic treatment.

On the contrary, if the calculated value is less than twice the value of said standard deviation, then, said tested individual is considered as not responding to said therapeutic treatment.

For establishing the first and second amounts, blood sample(s) of the tested individual are obtained by any conventional techniques known in the art, such as a needle or lancet, and a storage in a tank such as a tube, syringe, bottle or a flask.

The blood samples can be obtained either directly from the said tested individual or indirectly from a blood bag containing a blood sample from the said tested individual.

Advantageously, the blood samples used to establish the reference populations are obtained before the beginning of said therapeutic treatment.

Alternatively, the blood samples used to establish the reference populations are obtained at the beginning of the therapeutic treatment, i.e. when no treatment effect is apparent.

Advantageously, the blood samples used for the reference populations are obtained on the same day. Alternatively, the blood samples used for the reference populations are obtained on different days, advantageously at least one day apart, for example two days apart or three days apart.

Advantageously, at least three independent samples of said tested individual are used for said reference populations, more advantageously at least four blood samples, in particular at least five blood samples.

In another embodiment, said reference populations are obtained from at least one sample of at least two individuals, said at least two individuals being different from said tested individual.

Advantageously, the invention also relates to a method for the diagnosis of, advantageously the in vitro diagnosis of, i.e. for quantitatively evaluating, the response to a therapeutic treatment of a tested individual afflicted with a blood disorder affecting the deformability of the red blood cells and treated with said therapeutic treatment, said therapeutic treatment being directed to said blood disorder, method comprising the steps of:

a) determining a first amount of red blood cells having a tank-treading motion in a population of red blood cells, said population of red blood cells being obtained from a sample of said tested individual, b) calculating the value of the difference between a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, and said first amount of red blood cells having a tank-treading motion in a population of red blood cells, wherein said reference populations are obtained from at least one sample of at least two individuals, said at least two individuals being different from said tested individual and being in healthy condition, or free of any complication due to a condition or inter-current event, such that if said value of the difference is less than twice the value of said standard deviation, said tested individual is considered to be responsive to the said therapeutic treatment.

In such an embodiment, step b) relates to the following formula:

$$x = v_{control} - v_{sample}$$

wherein, x corresponds to the calculated value;

$v_{control}$ corresponds to the value of the second amount; and $v_{sample}$ corresponds to the value of the first amount.

According to this embodiment, the tested individual will be considered as responding to the treatment if there is no significant difference between the first and the second amounts.

In one embodiment, said reference populations are obtained from at least one sample of at least 10 individuals, advantageously of at least 20 individuals, of at least 30 individuals, of at least 50 individuals, of at least 100 individuals or of at least 200 individuals.

In one embodiment, the first amount is the calculated mean of the determined amount of red blood cells having a tank-treading motion obtained in populations of red blood cells.

Advantageously, the invention also relates to a method for the diagnosis of, advantageously the in vitro diagnosis of, i.e. for quantitatively evaluating, the response to a therapeutic treatment of a tested individual afflicted with a blood disorder affecting the deformability of the red blood cells and treated with said therapeutic treatment, said therapeutic treatment being directed to said blood disorder, method comprising the steps of:

a) determining a first amount being the calculated mean of the determined amount of red blood cells having a tank-treading motion obtained in populations of red blood cells, said populations of red blood cells being obtained from at least two samples of said tested individual, b) calculating the absolute value of the difference between said first amount of red blood cells having a tank-treading motion in populations of red blood cells, and a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, wherein said reference populations are obtained from at least two independent samples of said tested individual, before the beginning of said therapeutic treatment, such that if said value of the difference is greater or higher than twice the value of said standard deviation, said tested individual is considered to be responsive to the said therapeutic treatment.

After the said blood samples are obtained, the RBCs can be isolated from the other constituents of the blood, for example by centrifugation, or the blood sample can be directly diluted, for example in a solution of Dextran.

Afterwards, the RBCs are subjected to a shear flow and tracked using a visualisation means to determine the motion status of each RBC, such as tank-treading and other motions. The RBCs flow in a circulation means which can be a flow chamber, advantageously a microchannel, more advantageously a quartz flow chamber.

The said flow is generated by a generate means such as a pump, a syringe pump or a pressure controller.

Advantageously, the invention relates to the method as defined above, wherein for said determination of the first and second amounts is the red blood cells populations are subjected to a flow having a wall shear rate from 1 s$^{-1}$ to 50 s$^{-1}$, and a viscosity from 10$^{-3}$ to 0.5*10$^{-1}$ Pa·s.

By "from 1 s$^{-1}$ to 50 s$^{-1}$" it is meant in the invention 1 s$^{-1}$, 2 s$^{-1}$, 3 s$^{-1}$, 4 s$^{-1}$, 5 s$^{-1}$, 6 s$^{-1}$, 7 s$^{-1}$, 8 s$^{-1}$, 9 s$^{-1}$, 10 s$^{-1}$, 11 s$^{-1}$, 12 s$^{-1}$, 13 s$^{-1}$, 14 s$^{-1}$, 15 s$^{-1}$, 16 s$^{-1}$, 17 s$^{-1}$, 18 s$^{-1}$, 19 s$^{-1}$, 20 s$^{-1}$, 21 s$^{-1}$, 22 s$^{-1}$, 23 s$^{-1}$, 24 s$^{-1}$, 25 s$^{-1}$, 26 s$^{-1}$, 27 s$^{-1}$, 28 s$^{-1}$, 29 s$^{-1}$, 30 s$^{-1}$, 31 s$^{-1}$, 32 s$^{-1}$, 33 s$^{-1}$, 34 s$^{-1}$, 35 s$^{-1}$, 36 s$^{-1}$, 37 s$^{-1}$, 38 s$^{-1}$, 39 s$^{-1}$, 40 s$^{-1}$, 41 s$^{-1}$, 42 s$^{-1}$, 43 s$^{-1}$, 44 s$^{-1}$, 45 s$^{-1}$, 46 s$^{-1}$, 47 s$^{-1}$, 48 s$^{-1}$, 49 s$^{-1}$, 50 s$^{-1}$.

By "from 10$^{-3}$ to 0.5*10$^{-1}$ Pa·s" it is meant in the invention 0.01*10$^{-1}$ Pa·s, 0.02*10$^{-1}$ Pa·s, 0.03*10$^{-1}$ Pa·s, 0.04*10$^{-1}$ Pa·s, 0.05*10$^{-1}$ Pa·s, 0.06*10$^{-1}$ Pa·s, 0.07*10$^{-1}$ Pa·s, 0.08*10$^{-1}$ Pa·s, 0.09*10$^{-1}$ Pa·s, 0.1*10$^{-1}$ Pa·s, 0.11*10$^{-1}$ Pa·s, 0.12*10$^{-1}$ Pa·s, 0.13*10$^{-1}$ Pa·s, 0.14*10$^{-1}$ Pa·s, 0.15*10$^{-1}$ Pa·s, 0.16*10$^{-1}$ Pa·s, 0.17*10$^{-1}$ Pa·s, 0.18*10$^{-1}$ Pa·s, 0.19*10$^{-1}$ Pa·s, 0.2*10$^{-1}$ Pa·s, 0.21*10$^{-1}$ Pa·s, 0.22*10$^{-1}$ Pa·s, 0.23*10$^{-1}$ Pa·s, 0.24*10$^{-1}$ Pa·s, 0.25*10$^{-1}$ Pa·s, 0.26*10$^{-1}$ Pa·s, 0.27*10$^{-1}$ Pa·s, 0.28*10$^{-1}$ Pa·s, 0.29*10$^{-1}$ Pa·s, 0.3*10$^{-1}$ Pa·s, 0.31*10$^{-1}$ Pa·s, 0.32*10$^{-1}$ Pa·s, 0.33*10$^{-1}$ Pa·s, 0.34*10$^{-1}$ Pa·s, 0.35*10$^{-1}$ Pa·s, 0.36*10$^{-1}$ Pa·s, 0.37*10$^{-1}$ Pa·s, 0.38*10$^{-1}$ Pa·s, 0.39*10$^{-1}$ Pa·s, 0.4*10$^{-1}$ Pa·s, 0.41*10$^{-1}$ Pa·s, 0.42*10$^{-1}$ Pa·s, 0.43*10$^{-1}$ Pa·s, 0.44*10$^{-1}$ Pa·s, 0.45*10$^{-1}$ Pa·s, 0.46*10$^{-1}$ Pa·s, 0.47*10$^{-1}$ Pa·s, 0.48*10$^{-1}$ Pa·s, 0.49*10$^{-1}$ Pa·s, 0.5*10$^{-1}$ Pa·s.

Advantageously, the invention relates to the method as defined above, wherein the defined flow has a wall shear rate from 5 s$^{-1}$ to 19 s$^{-1}$. Advantageously, the defined flow has a viscosity from 0.15*10$^{-1}$ to 0.5*10$^{-1}$ Pa·s.

These flow conditions are advantageous for highlighting the variability of the amount of tank-treading RBCs of different red blood cell populations presenting different deformability properties when using a visualisation means for determining the type of motion of said RBCs for individual afflicted with a blood disorder affecting the deformability of the red blood cells.

During tracking, said RBCs are observed and counted by a visualisation means such as brightfield microscopy, by using an inverted microscope or optical lenses. The determination of the type of motion of each flowing red blood cells can be done directly with the eyes or carried out by an image processing technique or a computer program, as detailed further.

In an embodiment, the visualisation means are associated with a video recorder for recording the motion of the red blood cells. This embodiment allows analysing the images away from the place where the images are taken. More detail about such embodiment is provided below.

Advantageously, the invention relates to the method as defined above, wherein the blood disorder affecting the deformability of the red blood cells is selected from the group consisting of cell-sickle disease, thalassemia, acute coronary syndrome, bacterial sepsis, diabetes, malaria, stroke, paroxysmal nocturnal hemoglobinuria, haemolytic microangiopathy, red blood cell membrane disorders, enzymopathies, and hemoglobinopathies.

Briefly, thalassemia is a genetic disorder characterized by abnormal haemoglobin production, due to missing genes for α-globin (α-thalassemia) or β-globin (β-thalassemia). Depending on the severity, related to the number of missing genes, thalassemia symptoms can vary from mild anaemia to bone problems and children slow growth. RBCs of patients with β-thalassemia present an even higher shear modulus than healthy ones.

Acute coronary syndrome (ACS) is a syndrome (set of signs and symptoms) due to decreased blood flow in the coronary arteries such that part of the heart muscle is unable to function properly or dies. The most common symptom is chest pain, often radiating to the left shoulder or angle of the jaw, crushing, central and associated with nausea and sweating. Many people with acute coronary syndromes present with symptoms other than chest pain, particularly, women, older patients, and patients with diabetes mellitus.

Bacterial sepsis is caused by an immune response triggered by a bacterial infection. Common locations for the primary infection include lungs, brain, urinary tract, skin, and abdominal organs. Risk factors include young or old age, a weakened immune system from conditions such as cancer or diabetes, major trauma, or burns. An older method of diagnosis was based on meeting at least two systemic inflammatory response syndrome (SIRS) criteria due to a presumed infection.

Diabetes is a group of metabolic disorders in which there are high blood sugar levels over a prolonged period.

Malaria is most commonly transmitted by an infected female Anopheles mosquito. The mosquito bite introduces the parasites from the mosquito's saliva into a person's blood. The parasites travel to the liver where they mature and reproduce. Malaria is typically diagnosed by the microscopic examination of blood using blood films, or with antigen-based rapid diagnostic tests Methods that use the polymerase chain reaction to detect the parasite's DNA have been developed, but are not widely used in areas where malaria is common due to their cost and complexity.

Stroke is a medical condition in which poor blood flow to the brain results in cell death. There are two main types of stroke: ischemic, due to lack of blood flow, and haemorrhagic, due to bleeding. They result in part of the brain not functioning properly.

Paroxysmal nocturnal haemoglobinuria is a rare, acquired, life-threatening disease of the blood characterized by destruction of red blood cells by the complement system, a part of the body's innate immune system. This destructive process occurs due to the presence of defective surface proteins on the red blood cell, which normally functions to inhibit such immune reactions.

Thrombotic microangiopathy is a pathology that results in thrombosis in capillaries and arterioles, due to an endothelial injury. It may be seen in association with thrombocytopenia, anaemia, purpura and renal failure.

Membrane disorders are genetic disorders due to defects in one of the red cell membrane proteins.

Red cell Enzymopathies are genetic disorders due to defects in one of the red cell enzymes.

Hemoglobinopathies are genetic disorders due to defects in one of the globin chains.

The invention also relates to a method for the determination, preferably the in vitro determination, of the variation of the quality of red blood cells contained in a blood bag of a tested individual over time, the method comprising the steps of:

a) determining a first amount of red blood cells having a tank-treading motion in a population of red blood cells, said population of red blood cells being obtained from a sample of said blood bag, b) calculating the value of the difference between a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, and said first amount of red blood cells having a tank-treading motion in a population of red blood cells, wherein said reference populations are obtained either from at least two independent samples of said red blood cells contained in said blood bag recovered before the sample of the population of red blood cells of step a), or from at least one sample of at least two individuals, said at least two individuals being different from said tested individual, such that if said value is positive and greater or higher than twice the value of said standard deviation, then the red blood cells of said population obtained from a sample of said blood bag present a significant decrease of their quality compared to reference populations of red blood cells.

In such an embodiment, the comparison of the first and second amounts is carried out by calculating the value of the difference between the second and the first amount, and by comparing said calculated value to the value of the standard deviation of the red blood cells having a tank-treading motion obtained in the reference populations of red blood cells. Accordingly, the calculation has to be carried out in the established order.

In such an embodiment, step b) relates to the following formula:

$$x = v_{control} - v_{sample}$$

wherein, x corresponds to the calculated value;

$v_{control}$ corresponds to the value of the second amount; and $v_{sample}$ corresponds to the value of the first amount.

If the calculated value is a positive value and is greater or higher than twice the value of said standard deviation, then, the red blood cells of said population of said blood cells contained in said blood bag present a significant decrease of their quality compared to reference populations of red blood cells.

On the contrary, if the calculated value is less than twice the value of said standard deviation, then, the red blood cells of said population of said blood cells contained in said blood bag does not present a significant decrease of their quality compared to reference populations of red blood cells. According to such an evaluation, the said red blood cells contained in the blood bag can be transfused to a blood recipient.

Advantageously, said reference populations are obtained from at least one sample of at least two healthy individuals.

Alternatively, the reference populations are obtained directly from the tested individual, and not from the blood cells contained in a blood bag.

This aspect of the invention comes from the unexpected observation made by the inventors that the quality of the red blood cells contained in a blood bag can be easily and inexpensively determined by tracking the amount of tank-treading RBCs in a population of red blood cells.

Indeed, the quality of the red blood cells contained in a blood bag has been found to be related to the deformability properties of said red blood cells. Said deformability properties decrease according to the time spent by the red blood cells in the blood bag. Accordingly, measuring the amount of tank-treading RBCs in the population of red blood cells becomes a simple and inexpensively means to determine said quality of the red blood cells contained in the blood bag.

In one embodiment, the tested individual is an athlete.

Advantageously, the invention also relates to a method for the determination, preferably the in vitro determination, of the efficiency of a training of an athlete, the method comprising the steps of:

a) determining a first amount of red blood cells having a tank-treading motion in a population of red blood cells, said population of red blood cells being obtained from a sample of said athlete, b) calculating the value of the difference between said first amount of red blood cells having a tank-treading motion in a population of red blood cells, and a second amount being the calculated mean of the determined amount of red blood cells having a tank-treading motion obtained in reference populations of red blood cells, said calculated mean of the determined amount being obtained along with the value of the standard deviation of the red blood cells having a tank-treading motion obtained in the reference populations of red blood cells, wherein said reference populations are obtained from at least two independent samples of said athlete before the beginning of the training, such that if said value is positive and greater or higher than twice the value of said standard deviation, then the training is considered to be efficient.

In such an embodiment, the comparison of the first and second amounts is carried out by calculating the value of the difference between said first and second amounts, and by comparing said calculated value to the value of the standard deviation of the red blood cells having a tank-treading motion obtained in the reference populations of red blood cells. Accordingly, the calculation has to be carried out in the established order.

In such an embodiment, step b) relates to the following formula:

$$x = v_{sample} - v_{control}$$

wherein, x corresponds to the calculated value;

$v_{control}$ corresponds to the value of the second amount; and $v_{sample}$ corresponds to the value of the first amount.

If the calculated value is a positive value and is greater of higher than twice the value of said standard deviation, then the training is considered to be efficient.

The invention is also related to a device comprising a circulation means/member and a generate means for supplying a flow within said circulation means, the circulation means allowing the circulation of red blood cells, and further comprising a visualisation means for tracking the motion of said red blood cells in said circulation means, characterised in that the generate means is configured to supply a flow having a wall shear rate from 1 s$^{-1}$ to 50 s$^{-1}$, and a viscosity from 10$^{-3}$ Pa·s to 10$^{-1}$ Pa·s.

This aspect of the invention is an inexpensive and easy-to-implement device for the in vitro determination of the variability of the deformability property of red blood cells of an individual. This device is of great interest for predicting the occurrence of a vaso-occlusive crisis for a patient afflicted with cell-sickle disease, for monitoring the clinical status of individuals afflicted with a blood disorder affecting the deformability of the red blood cells, as well as for monitoring the physical abilities for athletes.

Advantageously, the said visualisation means is a light microscope, inverted or not, or a lens. The techniques of visualisation are brightfield, phase contrast or fluorescence microscopes. More advantageously, the brightfield microscope is configured to enlarge by at least 10 an image, for example by at least 15, at least 20, at least 30; at least 50.

Advantageously, the said generate means is a pump, a syringe pump or a pressure controller, configured to supply a flow having a wall shear rate from 1 s$^{-1}$ to 50 s$^{-1}$, and a viscosity from 10$^{-3}$ Pa·s to 10$^{-1}$ Pa·s.

By "from 1 s$^{-1}$ to 50 s$^{-1}$" it is meant in the invention 1 s$^{-1}$, 2 s$^{-1}$, 3 s$^{-1}$, 4 s$^{-1}$, 5 s$^{-1}$, 6 s$^{-1}$, 7 s$^{-1}$, 8 s$^{-1}$, 9 s$^{-1}$, 10 s$^{-1}$, 11 s$^{-1}$, 12 s$^{-1}$, 13 s$^{-1}$, 14 s$^{-1}$, 15 s$^{-1}$, 16 s$^{-1}$, 17 s$^{-1}$, 18 s$^{-1}$, 19 s$^{-1}$, 20 s$^{-1}$, 21 s$^{-1}$, 22 s$^{-1}$, 23 s$^{-1}$, 24 s$^{-1}$, 25 s$^{-1}$, 26 s$^{-1}$, 27 s$^{-1}$, 28 s$^{-1}$, 29 s$^{-1}$, 30 s$^{-1}$, 31 s$^{-1}$, 32 s$^{-1}$, 33 s$^{-1}$, 34 s$^{-1}$, 35 s$^{-1}$, 36 s$^{-1}$, 37 s$^{-1}$, 38 s$^{-1}$, 39 s$^{-1}$, 40 s$^{-1}$, 41 s$^{-1}$, 42 s$^{-1}$, 43 s$^{-1}$, 44 s$^{-1}$, 45 s$^{-1}$, 46 s$^{-1}$, 47 s$^{-1}$, 48 s$^{-1}$, 49 s$^{-1}$, 50 s$^{-1}$.

By "from 10$^{-3}$ to 0.5*10$^{-1}$ Pa·s" it is meant in the invention 0.01*10$^{-1}$ Pa·s, 0.02*10$^{-1}$ Pa·s, 0.03*10$^{-1}$ Pa·s, 0.04*10$^{-1}$ Pa·s, 0.05*10$^{-1}$ Pa·s, 0.06*10$^{-1}$ Pa·s, 0.07*10$^{-1}$ Pa·s, 0.08*10$^{-1}$ Pa·s, 0.09*10$^{-1}$ Pa·s, 0.1*10$^{-1}$ Pa·s, 0.11*10$^{-1}$ Pa·s, 0.12*10$^{-1}$ Pa·s, 0.13*10$^{-1}$ Pa·s, 0.14*10$^{-1}$ Pa·s, 0.15*10$^{-1}$ Pa·s, 0.16*10$^{-1}$ Pa·s, 0.17*10$^{-1}$ Pa·s, 0.18*10$^{-1}$ Pa·s, 0.19*10$^{-1}$ Pa·s, 0.2*10$^{-1}$ Pa·s, 0.21*10$^{-1}$ Pa·s, 0.22*10$^{-1}$ Pa·s, 0.23*10$^{-1}$ Pa·s, 0.24*10$^{-1}$ Pa·s, 0.25*10$^{-1}$ Pa·s, 0.26*10$^{-1}$ Pa·s, 0.27*10$^{-1}$ Pa·s, 0.28*10$^{-1}$ Pa·s, 0.29*10$^{-1}$ Pa·s, 0.3*10$^{-1}$ Pa·s, 0.31*10$^{-1}$ Pa·s, 0.32*10$^{-1}$ Pa·s, 0.33*10$^{-1}$ Pa·s, 0.34*10$^{-1}$ Pa·s, 0.35*10$^{-1}$ Pa·s, 0.36*10$^{-1}$ Pa·s, 0.37*10$^{-1}$ Pa·s, 0.38*10$^{-1}$ Pa·s, 0.39*10$^{-1}$ Pa·s, 0.4*10$^{-1}$ Pa·s, 0.41*10$^{-1}$ Pa·s, 0.42*10$^{-1}$ Pa·s, 0.43*10$^{-1}$ Pa·s, 0.44*10$^{-1}$ Pa·s, 0.45*10$^{-1}$ Pa·s, 0.46*10$^{-1}$ Pa·s, 0.47*10$^{-1}$ Pa·s, 0.48*10$^{-1}$ Pa·s, 0.49*10$^{-1}$ Pa·s, 0.5*10$^{-1}$ Pa·s.

Advantageously, the said circulation means is a flow chamber, advantageously a microchannel, more advantageously a quartz flow chamber.

In one embodiment, the device of the invention is configured to be held by the hand. In another embodiment, the device of the invention is configured to be laid on a table. Therefore, in both cases, the device can be used by an individual alone at home, or by a physician at its office.

In one embodiment, the device further comprises a collecting means for collecting a blood sample, advantageously by a fingerprick. Said collecting means can be a needle. Advantageously, the volume of the blood sample that the collecting means is configured to collect at least 1 μl, for example 2 μl, 3 μl, 5 μl. Advantageously, the collecting means and the circulation means are connected by a channel.

In the one embodiment, the visualisation means is associated with a recording means, such as a camera, for recording images of the motion of the red blood cells. The recording means acquires and records data coming from the visualisation means, advantageously in numerical format. The recording means can be associated with a memory for the storage of the captured images. The combined visualisation and recording means are configured to define a red blood cell by several pixels, advantageously by at least 20 pixels.

Advantageously, the device further comprises a computer program stored on a memory and configured for analysing the images recorded by the recording means and determining the red blood cells having a tank-treading motion among a population of red blood cells from a tested blood sample of said individual.

Advantageously, the device comprises a display, such as a screen, for displaying the number of red blood cells having a tank-treading motion determined by the computer program.

It is also possible to analyse the images of the motion of the red blood cells away from the device. In that respect, the device can comprise an emission means, such as an antenna, for collecting the images from the recording means and sending them to a computer. Advantageously, said computer comprises a computer program for analysing the images receiving from the device and determining the red blood cells having a tank-treading motion among a population of red blood cells from a tested blood sample of said individual.

All the elements of the device can be disposable elements. Advantageously, the flow chamber is a disposable element.

The invention is also related to an apparatus comprising:
a device comprising a circulation means and a generate means for supplying a flow within said circulation means, the circulation means allowing the circulation of red blood cells, and further comprising a visualisation means for monitoring the motion of said red blood cells in said circulation means, wherein the generate means is configured to supply a flow having a wall shear rate from 1 s$^{-1}$ to 50 s$^{-1}$, and a viscosity from 10$^{-3}$ Pa·s to 10$^{-1}$ Pa·s, wherein the visualisation means is associated with a recording means for recording images of the motion of the red blood cells, and wherein the device also comprises an emission means for collecting the information from the camera and sending them to a computer,
a computer provided with a reception antenna for receiving the images sent by the emission means of the said device, and a computer program for analysing the images receiving from the device and determining the red blood cells having a tank-treading motion among a population of red blood cells from a tested blood sample of said individual.
Advantageously, the computer is a cellular phone.

LEGEND TO THE FIGURES

FIG. 1 is a schematic view of the three regimes of motion of RBC. Time sequences schematically representing the projected shapes in the shear plane of RBCs moving from left to right in a shear flow: tumbling (a), rolling (b) and tank-treading (c). The black dots on the RBCs together with arrow display the motion of a membrane element on the RBCs surface.

FIG. 2 is a schematic of the tank-treading experiment comprising a flow chamber where RBCs move and a microscope associated with a camera for recording images of said motion. The RBC stabilized motion is acquired at the end of the flow chamber (frame: 660×571 μm$^2$) after they have moved for about 5 mm at a constant shear rate $\dot{\gamma}$. Left scale bar: 10 µm; right scale bar: 50 µm. 21-fps movies are analysed to classify RBC motion into three categories: Tank-Treading (top), Rolling (middle) and Flip-Flopping (bottom).

FIGS. 3A-3D represent the sensitivity of the proportion of RBCs in the tank-treading regime in the RBCs population from patients afflicted with sickle cell disease and healthy individuals. FIG. 3A is a graph representing the evolution of the ratio of RBCs found to be tank-treading $f_{TT}$ (Y-axis from 0.2 to 1) in the whole RBCs population as a function of the shear rate $\dot{\gamma}$ (X-axis from 0 to 16) for three healthy samples (open circle symbols): from top to bottom HbAA11, HbAA3, HbAA4 from Table 1) and three SCD samples (solid circle symbols: from top to bottom HbSS31, HbSS9, HbSS8 from Table 1. FIG. 3B is a graph representing box plots of $f_{TT}$ (Y-axis) at a constant shear rate of 10 s$^{-1}$ for nine healthy samples (individual HbAA 3-12 from Table 1) on the left box plot, and on the middle box plot fourteen SCD (patients HbSS 4-17 from Table 1), and on the right box plot 15 heterozygote thalassemic patients (HbpA3-17 from the Table 1). FIG. 3C is a graph representing the Evolution of $f_{TT}$ (Y-axis) at a constant shear rate of 15 s$^{-1}$ as function of RBC mean density (X-axis) for 2 healthy (hollow circle symbols: individuals HbAA 1 and 5 from Table 1) and 2 SCD (solid circle symbols: patients HbSS 3 and 16 from Table 1) samples. FIG. 3D is a graph representing the evolution of $f_{TT}$ (Y-axis) at a constant shear rate of 15 s$^{-1}$ as function of RBC state of dehydration (X-axis) for one healthy (hollow circle symbols: individual HbAA 6 from Table 1, h) and one SCD ((solid circle symbols: patient HbSS 17 from Table 1) samples. Dehydration is achieved by using a hyper-osmotic external buffer (>300 mOsm).

FIGS. 4A-4C represent the evolution of the proportion of tank-treading RBCs in the RBCs population in 7 SCD patients during vaso-occlusive events. Blood samples were harvested from patients during their stay at the hospital due to the occurrence of a crisis. For each graph is considered the following representation: solid circle symbols correspond to patient HbSS 22 from Table 1; solid square symbols correspond to patient HbSS 24 from Table 1; up triangle symbols represent patient HbSS 25 from Table 1; diamond symbols represent patient HbSS 19 from Table 1; criss-cross square symbols represent patient HbSS 20 from Table 1; down triangle symbols represent patient HbSS 23 from Table 1; hollow circle symbols represent patient HbSS 21 from Table 1. FIG. 4A is a graph representing the temporal evolution of $f_{TT}$ (Y-axis from 0.5 to 1) during and after crisis for five patients who had a single crisis. The X-axis (from −8 to 10) represents the days of hospitalisation for the vaso-occlusive crisis with 0 corresponding to the moment of hospitalisation. For patient HbSS 24, a blood sample has been obtained 6 days before being hospitalized for the vaso-occlusive crisis. FIG. 4B is a graph representing the temporal evolution of $f_{TT}$ (Y-axis from 0.5 to 1) during and after crisis for two patients who underwent a second crisis during their stay. The X-axis (from 0 to 18) represents the days of hospitalisation for a vaso-occlusive crisis with 0 corresponding to the moment of hospitalisation. FIG. 4C is a graph representing the $f_{TT}$ temporal evolution compiling data from (A) and (B) with abscissa and ordinates shifted for each curve: 0-abscissa is the estimated time of maximum $f_{TT}$ and 0-ordinate is the estimated base level.

FIGS. 5A-5B represent a device according to the invention. FIG. 5A is a top view and FIG. 5B is a front view. In FIGS. 5A and 5B, the different elements are represented transparently.

FIG. 6 is a histogram which represents the baseline for the ratio of RBCs that were found to tank-tread $f_{TT}$ (Y-axis from 0 to 1) for 9 homozygous SCD patients (X-axis from 1 to 9) over 6 months. For patient 1, 20 samples were recovered. For patient 2, 17 samples were recovered. For patient 3, 19 samples were recovered. For patient 4, 21 samples were recovered. For patient 5, 17 samples were recovered. For patient 6, 20 samples were recovered. For patient 7, 22 samples were recovered. For patients 8 and 9, 11 samples were recovered respectively. For each histogram is also represented the standard deviation. Each measurement was performed at a shear rate $\dot{\gamma}$ of 10 s$^{-1}$.

FIG. 7 is a graphical representation of the ratio of RBCs found to tank-tread $f_{TT}$ (Y-axis from 0 to 1) as a function of time (X-axis in days) for patient 1 represented in FIG. 6. Each dot represents a measurement on a sample of the patient.

FIG. 8 is a graphical representation of the ratio of RBCs found to tank-tread $f_{TT}$ (Y-axis from 0 to 1) as a function of time (X-axis in days) for patient 2 represented in FIG. 6. Each dot represents a measurement on a sample of the patient.

Figure 16:
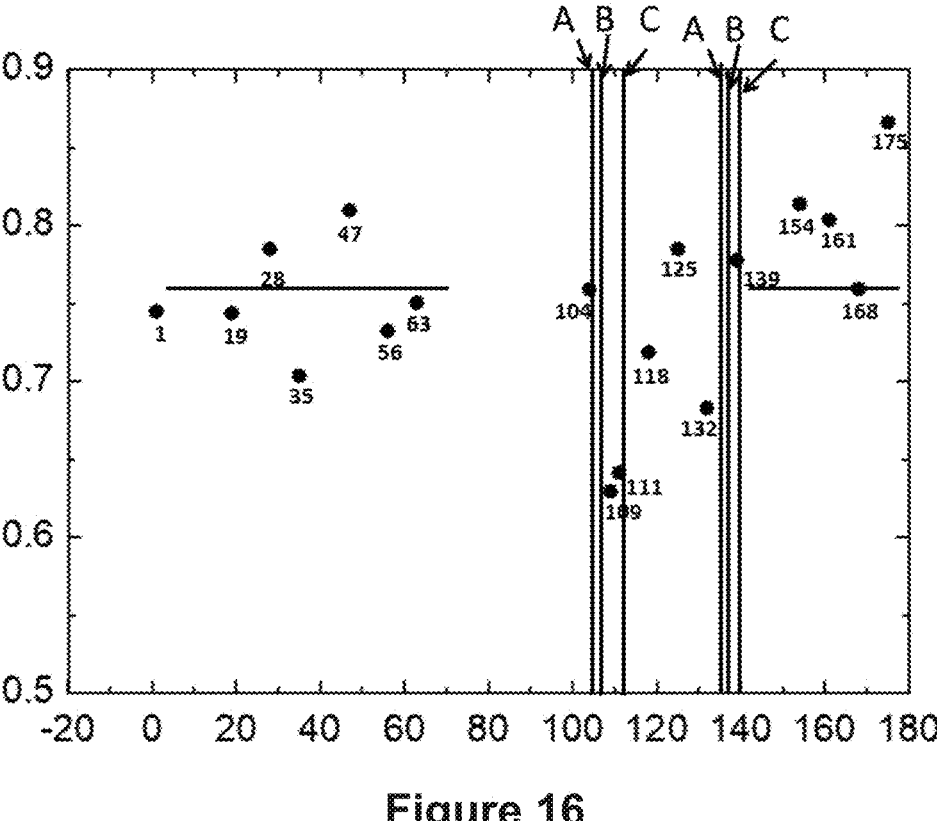

FIG. 16 represents the ratio of RBCs found to tank-tread $f_{TT}$ (Y-axis from 0 to 1) as a function of time (X-axis in days) for a homozygous SCD patient (patient 10). Each dot represents a measurement on a sample of the patient. Each measurement performed at a shear rate $\dot{\gamma}$ of 10 s$^{-1}$. The horizontal solid lines represent the mean $f_{TT}$ value for an "out of crisis" period. The vertical line A represents the day when the patient's pain is a sign of crisis; the vertical line B represents the day of hospitalization; and the vertical line C represents the day of discharge from the hospital.

Figure 17:
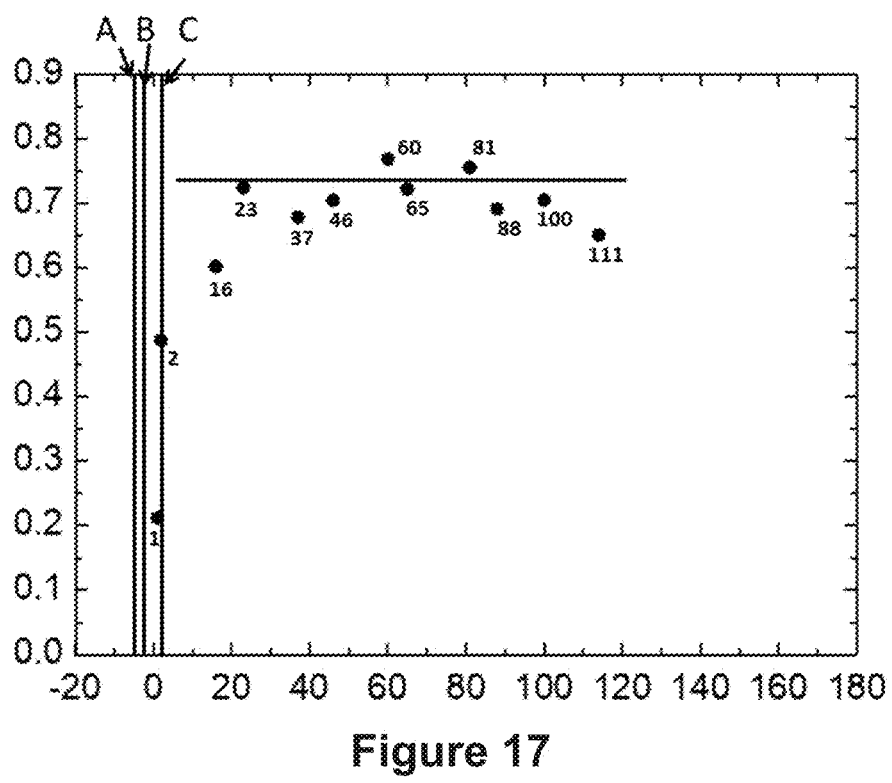

FIG. 17 represents the ratio of RBCs found to tank-tread $f_{TT}$ (Y-axis from 0 to 1) as a function of time (X-axis in days) for a homozygous SCD patient (patient 11). Each dot represents a measurement on a sample of the patient. Each measurement was performed at a shear rate $\dot{\gamma}$ of 10 s$^{-1}$. The horizontal solid lines represent the mean $f_{TT}$ value for an "out of crisis" period. The vertical line A represents the day when the patient's pain is a sign of crisis; the vertical line B represents the day of hospitalization; and the vertical line C represents the day of discharge from the hospital.

Figure 18:
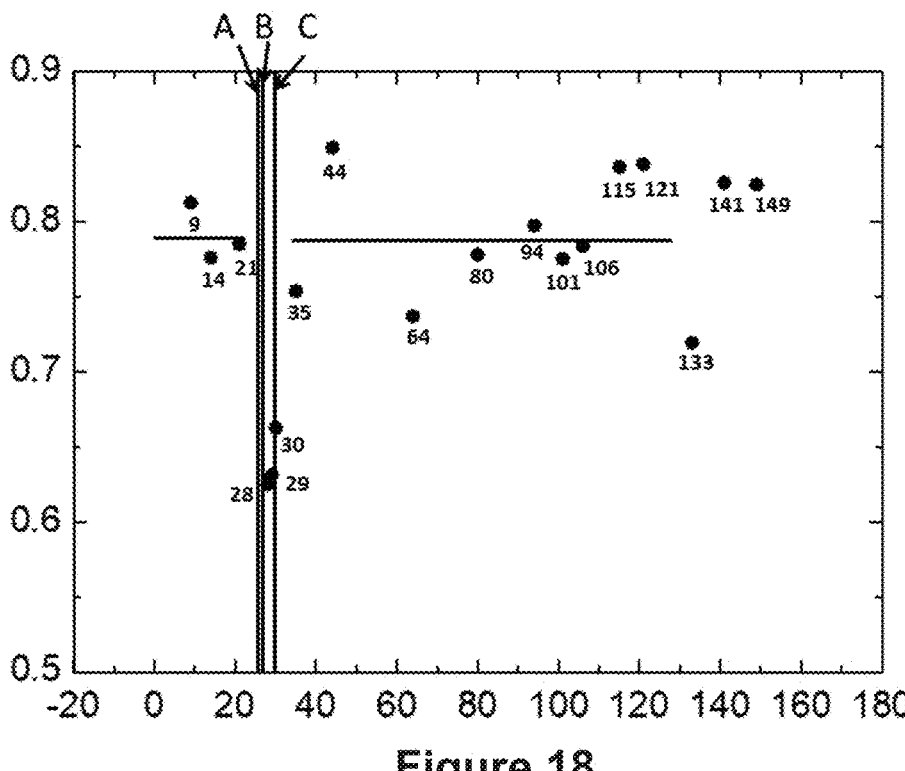

FIG. 18 represents the ratio of RBCs found to tank-tread $f_{TT}$ (Y-axis from 0 to 1) as a function of time (X-axis in days) for a homozygous SCD patient (patient 12). Each dot represents a measurement on a sample of the patient. Each measurement was performed at a shear rate $\dot{\gamma}$ of 10 s$^{-1}$. The horizontal solid lines represent the mean $f_{TT}$ value for an "out of crisis" period. The vertical line A represents the day when the patient's pain is a sign of crisis; the vertical line B represents the day of hospitalization; and the vertical line C represents the day of discharge from the hospital.

Figure 5A:
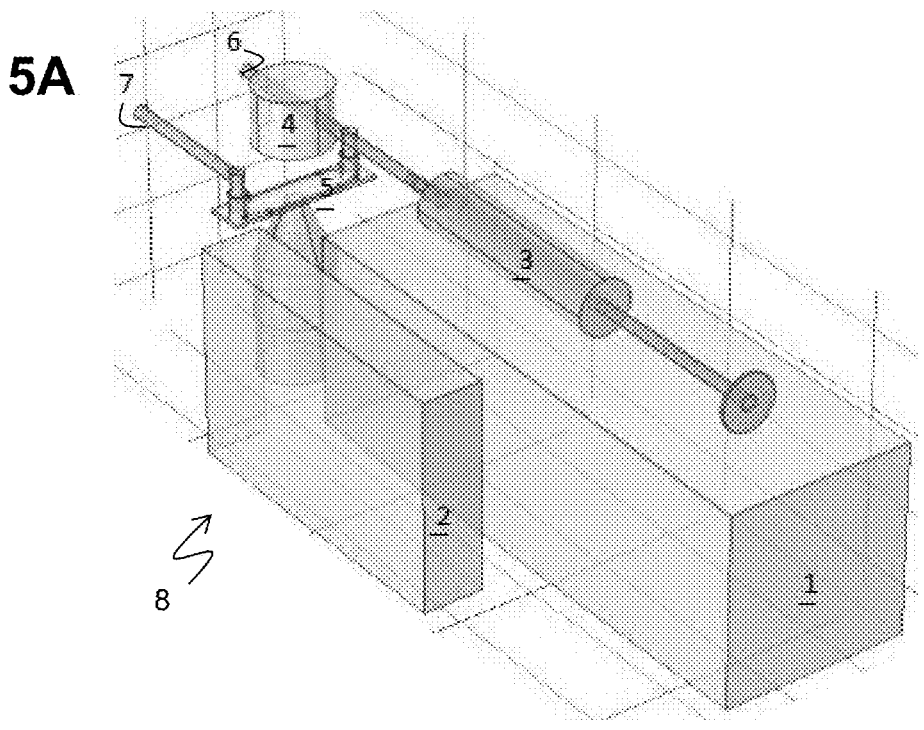
Figure 5B:
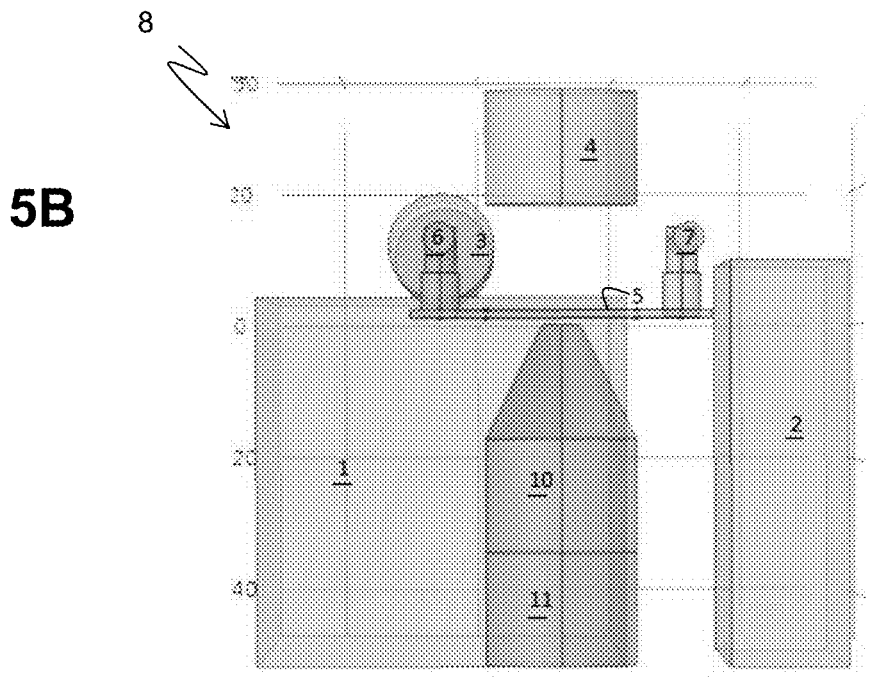
Figures 9, 10, 11, 12, 13, 14:
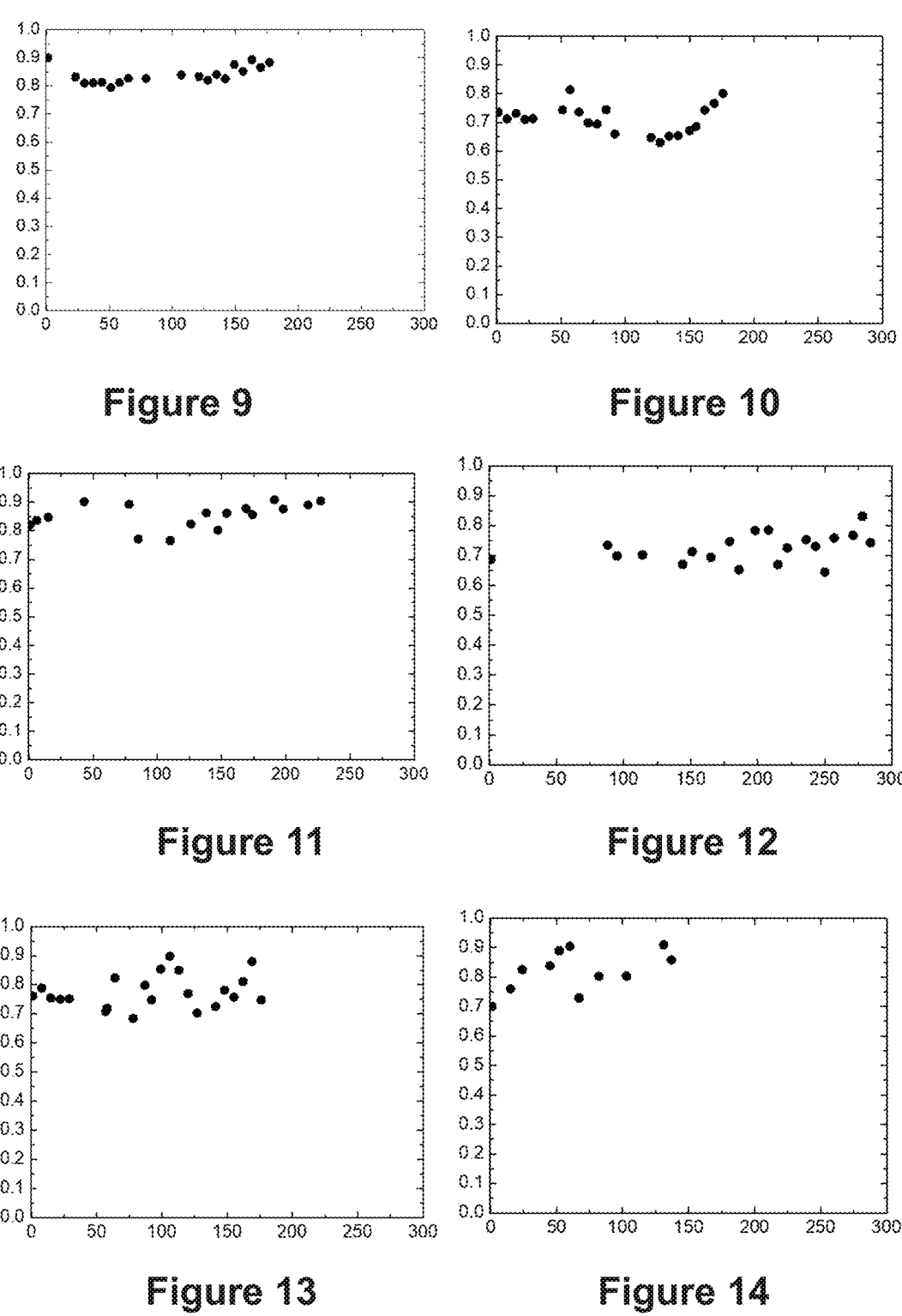
FIG. 9 is a graphical representation of the ratio of RBCs found to tank-tread $f_{TT}$ (Y-axis from 0 to 1) as a function of time (X-axis in days) for patient 3 represented in FIG. 6. Each dot represents a measurement on a sample of the patient.
FIG. 10 is a graphical representation of the ratio of RBCs found to tank-tread $f_{TT}$ (Y-axis from 0 to 1) as a function of time (X-axis in days) for patient 4 represented in FIG. 6. Each dot represents a measurement on a sample of the patient.
FIG. 11 is a graphical representation of the ratio of RBCs found to tank-tread $f_{TT}$ (Y-axis from 0 to 1) as a function of time (X-axis in days) for patient 5 represented in FIG. 6. Each dot represents a measurement on a sample of the patient.
FIG. 12 is a graphical representation of the ratio of RBCs found to tank-tread $f_{TT}$ (Y-axis from 0 to 1) as a function of time (X-axis in days) for patient 6 represented in FIG. 6. Each dot represents a measurement on a sample of the patient.
FIG. 13 is a graphical representation of the ratio of RBCs found to tank-tread $f_{TT}$ (Y-axis from 0 to 1) as a function of time (X-axis in days) for patient 7 represented in FIG. 6. Each dot represents a measurement on a sample of the patient.
FIG. 14 is a graphical representation of the ratio of RBCs found to tank-tread $f_{TT}$ (Y-axis from 0 to 1) as a function of time (X-axis in days) for patient 8 represented in FIG. 6. Each dot represents a measurement on a sample of the patient.
Figure 15:
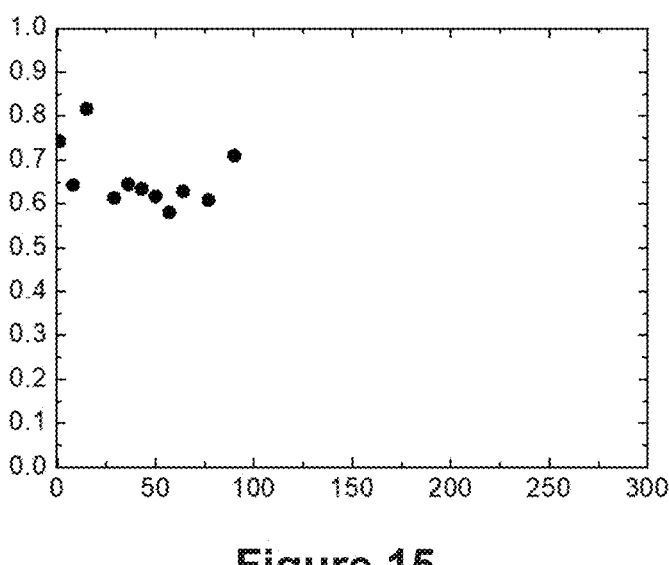
FIG. 15 is a graphical representation of the ratio of RBCs found to tank-tread $f_{TT}$ (Y-axis from 0 to 1) as a function of time (X-axis in days) for patient 9 represented in FIG. 6. Each dot represents a measurement on a sample of the patient.

Hereafter it is described one example of such a device according to FIGS. 5A and 5B, and its method of operating.

A fingertip prick blood drop is first recovered on the finger of a tested individual and diluted in 1.5 ml of Dextran solution. The recovery can be done by a capillary tube (not shown).

Then, the blood is mechanically mixed with the Dextran solution by using a syringe 3 connected to the said capillary tube. The solution of dextran can be conditioned in unidose. The syringe is then filled in with the mixed RBC suspension.

Subsequently, the syringe 3 is set on a syringe pump 1 in a device 8 and connected to a flow chamber 5. The syringe pump 1 comprises a motor (not shown) for pushing the RBC suspension into the flow chamber 5 at a given viscosity and shear rate.

Afterwards, the device 8 is switched on which causes the activation of the motor of the syringe pump 1. Accordingly, said syringe pump 1 pushes the blood suspension contained within the syringe 3 into the flow chamber 5. Accordingly, the blood suspension will flow through the flow chamber 5 at the given shear rate and viscosity. The syringe pump 1 is configured to supply within the flow chamber 5 a flow having a wall shear rate from 1 s$^{-1}$ to 50 s$^{-1}$, and a viscosity from 10$^{-3}$ Pa·s to 10$^{-1}$ Pa·s.

The device 8 comprises a light 4, optical lenses 10, and a camera 11 which are switched on with the pump's motor to acquire a video of flowing red blood cells. The recorded video is stored in a computer 2. This computer 2 can be placed within the device 8 as shown in the figure or can be placed away. For example, the computer can be a smartphone.

The computer comprises an adequate software to analyze these videos. Different analyses can be done and include, but are not limited to, the percentage of the red blood cell with a tank-treading motion, pictograms, and recommendations.

The pictograms can represent a colour code, which is a function of the result of the analysis, such as red, yellow, green, with red meaning having rest and contact a doctor, yellow meaning to repeat the analysis within 24 hours and green meaning that the result of the analysis is good.

The recommendations can be to have rest, to repeat the analysis within 24 hours or to contact a doctor, in function of the result of the analysis.

The results of the analysis (% TT, pictogram, recommendation) are displayed on a screen. This screen can be part of the device 8, as shown in the FIGS. 5A and 5B, or be placed away. In case the computer is a smartphone, the said screen would be the screen of the smartphone.

The results can be stored in the computer and potentially, sent to a medical centre or a doctor.

The device 8 can further comprise an outlet 7 connected at the end of the flow chamber 5, in order to recover the RBC solution that has flowed through the chamber 5.

An inlet 6 can advantageously be connected to the tip of the syringe 3. In such a case, the syringe 3 is directly filled in within the device, so that there is no need to put the syringe 3 out of the device.

EXAMPLE

Methods

Buffers dextran (from Leuconostoc menseteroides, 2000 kDa, Sigma-Aldrich) was solubilized at 9% (wt/wt) in homemade PBS (osmolarity: 295±5 mOsm, pH: 7.4) by stirring at 50° C. for at least 2 hours. The dextran solution had a viscosity $\eta_o$=39.2±0.7 10-3 Pa-s at a temperature of 20° C. and its density approximately matched RBC density, thus preventing cell sedimentation. Dehydration experiments were conducted using hyper-osmotic PBS buffers (up to 600 mOsm) which were prepared by concentrating all reagents in the PBS proportionally.

Blood Samples

Most tested blood specimens are a subset of residual samples referred to the Department of Genetics (Hôpital de La Timone, Marseille, France) for routine tests (haematological parameters for each individual/patient are given in Table 1 below). Blood was obtained from thirty homozygous subjects with SCD (HbSS), eight SCD patients during a vaso-occlusive event requiring hospitalization (Crisis), HbSS patients were selected preferentially with high % HbS (non-transfused) and low % foetal Hb (HbF), and fifteen heterozygous patients with thalassemia. Blood samples were mixed with EDTA when harvested and RBCs were then isolated within 24 hours by three consecutive washing steps in SAG-mannitol (SAGM, EFS, France) at a centrifugation rate of 500 g (10 min at 4° C.), then suspended in SAGM (haematocrit, Hct: 50%) for storage at 4° C., and used within 7 days. The blood samples were used as follows: individual HbAA 3 to 12, patients HbSS 4 to 17 and thalassemic patients were used in tank-treading experiments; Patients HbSS 8 and 19 to 25 were followed during vaso-occlusive events requiring hospitalisation.

TABLE 1

| | | | haematological parameters of tested subjects | | | | |
|---|---|---|---|---|---|---|---|
| Patient/ Individual | Age (years) | % HbS | % HbF | Hct (L/L) | MCV (μm$^3$) | MCH (pg/cell) | MCHC (g/dL) |
| Range | N/A | N/A | N/A | 0.37-0.47 | 80-98 | 27-32 | 30-36.5 |
| HbSS 1 | 22 | 84 | 7.1 | 0.21 | 81.6 | 29.8 | 36.5 |
| HbSS 2 | 33 | 72.4 | 18.1 | 0.19 | 101 | 38 | 37.6 |

TABLE 1-continued

| | | | | | | | |
|---|---|---|---|---|---|---|---|
| | | | haematological parameters of tested subjects | | | | |
| Patient/ Individual | Age (years) | % HbS | % HbF | Hct (L/L) | MCV ($\mu m^3$) | MCH (pg/cell) | MCHC (g/dL) |
| HbSS 3 | 36 | 84.6 | 7.8 | 0.21 | 89.2 | 32.3 | 36.2 |
| HbSS 4 | 34 | 82 | 9.2 | 0.2 | 85.9 | 30.3 | 35.3 |
| HbSS 5 | 16 | 78.9 | 11.1 | 0.24 | 83.8 | 29.9 | 35.7 |
| HbSS 6 | 14 | 78.9 | 12.1 | 0.21 | 79.3 | 26.7 | 33.6 |
| HbSS 7 | 49 | 48.3 | 33 | 0.14 | 112 | 41.6 | 37.1 |
| HbSS 8 | 31 | 71.3 | 11.9 | 0.21 | 80.9 | 24.6 | 30.4 |
| HbSS 9 | 32 | 71.1 | 17.3 | 0.21 | 75.1 | 26.3 | 35 |
| HbSS 10 | Missing | 63.8 | 24.9 | 0.22 | 89.7 | 32.2 | 35.9 |
| HbSS 11 | Missing | 77.2 | 13.6 | 0.26 | 100.8 | 35.3 | 35 |
| HbSS 12 | 22 | 84.5 | 4.6 | 0.23 | 67.9 | 23.3 | 34.3 |
| HbSS 13 | 19 | 69.7 | 18.2 | 0.29 | 83.9 | 28.1 | 33.4 |
| HbSS 14 | 41 | 73 | 10.8 | 0.28 | 113.4 | 38.9 | 34.3 |
| HbSS 15 | 6 | 85.4 | 6.1 | 0.19 | 92.3 | 33.7 | 36.5 |
| HbSS 16 | Missing | 83.9 | 3.4 | 0.19 | 90 | 32 | 35.6 |
| HbSS 17 | 15 | 88.3 | 3.4 | 0.21 | 67.1 | 23.2 | 34.6 |
| HbSS 18 | 32 | 71 | 11.3 | 0.18 | 91.5 | 32.3 | 35.3 |
| HbSS 19 | 35 | 78.2 | 13.2 | 0.26 | 94.6 | 33.7 | 35.6 |
| HbSS 20 | 23 | 74.1 | 7.4 | 0.25 | 86 | 32.1 | 37.3 |
| HbSS 21 | 20 | 73.4 | 13.7 | 0.18 | 71.5 | 23.6 | 33 |
| HbSS 22 | 25 | 55.2 | 1.1 | 0.23 | 70.9 | 23.9 | 33.6 |
| HbSS 23 | 26 | 75.3 | 4.3 | 0.27 | 88.7 | 30.7 | 34.6 |
| HbSS 24 | 33 | 24.1 | 3.1 | 0.24 | 80.5 | 25.9 | 32.2 |
| HbSS 25 | 18 | 76 | 13.9 | 0.23 | 86.8 | 33.2 | 38.3 |
| HbSS 26 | Missing | Missing | Missing | Missing | Missing | Missing | Missing |
| HbSS 27 | 51 | 66.3 | 20.2 | 0.23 | 107.1 | 38.2 | 35.7 |
| HbSS 28 | 51 | 68.1 | 19.5 | 0.23 | 107.1 | 38.2 | 35.7 |
| HbSS 29 | 51 | 74.8 | 13 | 0.22 | 96.1 | 35.8 | 37.3 |
| HbSS 30 | 21 | 67.5 | 18.7 | 0.18 | 80.3 | 24.3 | 30.3 |
| HbSS 31 | missing | 71.8 | 15.9 | missing | missing | missing | missing |
| HbβS 1 | 10 | 72 | 9.9 | 0.24 | 69.9 | 23.2 | 33.2 |
| HbβS 2 | 14 | 72.4 | 14.7 | 0.22 | 65.2 | 21.2 | 32.6 |
| HbAA 1 | 39 | 0 | 0.8 | 0.39 | 88 | 30 | 34 |
| HbAA 2 | 47 | 0 | 0.5 | 0.42 | 82.5 | 28.6 | 34.6 |
| HbAA 3 | 35 | 0 | 0.5 | 0.42 | 86 | 30 | 34.4 |
| HbAA 4 | 43 | 0 | 1.1 | 0.35 | 78 | 27 | 34.4 |
| HbAA 5 | 13 | 0 | 0.4 | 0.35 | 81.6 | 27.9 | 34.2 |
| HbAA 6 | 22 | 0 | 0.6 | 0.3 | 92.7 | 33.1 | 35.7 |
| HbAA 7 | 34 | 0 | 0.5 | 0.42 | 86 | 30 | 34.4 |
| HbAA 8-11 | | | Volunteers, no information | | | | |
| HbβA 1 | | | Volunteer, no information | | | | |
| HbβA 2 | 59 | 0 | 0.5 | 0.42 | 63 | 20.1 | 31.9 |
| HbβA 3 | Missing | 0 | 1.1 | Missing | Missing | Missing | Missing |
| HbβA 4 | Missing | 0 | 3.3 | Missing | Missing | Missing | Missing |
| HbβA 5 | Missing | 0 | 1.2 | Missing | Missing | Missing | Missing |
| HbβA 6 | Missing | 0 | 10.1 | Missing | Missing | Missing | Missing |
| HbβA 7 | Missing | 0 | 1.2 | Missing | Missing | Missing | Missing |
| HbβA 8 | Missing | 0 | 1.7 | Missing | Missing | Missing | Missing |
| HbβA 9 | Missing | 0 | 1.4 | Missing | Missing | Missing | Missing |
| HbβA 10 | Missing | 0 | 0.8 | Missing | Missing | Missing | Missing |
| HbβA 11 | Missing | 0 | 0.7 | Missing | Missing | Missing | Missing |
| HbβA 12 | Missing | 0 | 0.7 | Missing | Missing | Missing | Missing |
| HbβA 13 | Missing | 0 | 1 | Missing | Missing | Missing | Missing |
| HbβA 14 | Missing | 0 | 1.1 | Missing | Missing | Missing | Missing |
| HbβA 15 | Missing | 0 | unknown | Missing | Missing | Missing | Missing |
| HbβA 16 | Missing | 0 | 1.3 | Missing | Missing | Missing | Missing |
| HbβA 17 | Missing | 0 | 80.7 | Missing | Missing | Missing | Missing |
| Hbββ 1 | Missing | 0 | 75.7 | Missing | Missing | Missing | Missing |

By "Hct", it is meant in the invention the haematocrit which is the volume percentage of red blood cells in blood.

By "MCV", it is meant in the invention the mean corpuscular volume, or mean cell volume, which is a measure of the average volume of a read blood cell.

By "MCH", it is meant in the invention the man corpuscular haemoglobin, or "mean cell haemoglobin", which is the average mass of haemoglobin per red blood cell in aa sample of blood.

By "MCHC", it is meant in the invention the mean corpuscular haemoglobin concentration, a measure of the concentration of haemoglobin in a given volume of packed red blood cells.

Flow Experiments and Microscopy

Flow experiments were performed as described previously (FIG. 2). Briefly, RBCs stored at 50% Hct were diluted ($\approx$500×) in a solution of Dextran and injected in a parallelepiped quartz flow chamber ($50 \times 10 \times 0.9$ mm$^3$) mounted on an inverted microscope (DMIRB, Leica). The fluid was driven by a syringe pump (11 Plus, Harvard Apparatus) at increasing wall shear rates $\dot{\gamma}$ starting from 1 s$^{-1}$ up to 20 s$^{-1}$.

First Experiment

RBCs were observed within 65 $\mu$m from the bottom wall (zone of constant shear rate) in brightfield microscopy (20× objective) along the direction of the flow gradient. Images were recorded at 21 fps with a camera and processed semi-automatically using Matlab home-made routines. Each RBC passing in the observation field of the microscope was individually tracked by a custom-made Matlab program and the projection of its shape in the observation plane was detected and fitted by an ellipse to identify its regime of motion.

The tank-treading motion of the red blood cells using custom-made Matlab tracking programs is determined as it follows:

The determination is carried out in two parts.

Part 1

This part corresponds to the pre-categorization of the MATLAB routine that sorts all cells into different categories: speed, remove, multiple, others, axis, size, suspicious, track correlation, area and tank treading.

The Criteria for Each Category are:

Speed: the cell falls within this category if the cell moves more than twice as fast than the average between two frames. The speed of one cell is calculated by the program by measuring the displacement of the cell between two frames. This is done for each cell and for its entire trajectory;

Remove: the cell falls within this category if the cell trajectory across the observation field of the microscope is less than seven frames long;

Multiple: the cell falls within this category if the trajectory of two cells overlap;

Others: the cell falls within this category if the length ratio of the minor axis divided by the major axis of the cell is less than 0.5. In such a case, the motion of the cell corresponds either to rolling or to tumbling;

Axis: the cell falls within this category if the ratio between the main geometrical axes of the cell lies between 0.5 and 0.7. This implies in such a case, that the cell maintains a shape that is not characteristic for the typical motion types);

Size: the cell falls within this category if the major axis of the cell is smaller than a defined threshold (10 for instance). This threshold is given in pixel and can be adjusted to object size and used equipment;

Suspicious: the cell falls within this category if the cell presents an oddly shaped. This is carried out by comparing the original black and white image of the cell with a modified image of the same cell (the interior of the cell gets filled white, if the borders of the cell are well defined, the exterior region remains unchanged, if not, the whole picture turns white) to ensure integrity of cell boundaries;

Track correlation: the cell falls within this category if its motion is not consistent. This is carried out by calculating a mean and standard deviation for each cross correlation and normalizing them to 1. Since the cells move across the observation field of the microscope according to a line direction with nearly constant speed, the trajectory of the cell is very predictable and can be easily correlated by localizing the cell on frame n and looking for the cell on frame n+1 at the distance travelled between two frames. The intensity (arbitrary unit within the program) of every pixel of the cell is compared with the corresponding pixel of the cell in the next frame using an internal MATLAB algorithm giving an output between 0 (no correlation) to 1 (100% correlation) representing the comparability of the two images without unit. This is done for all images of the trajectory of each cell. If the mean of the comparability for all images of one trajectory of one cell is below 0.5 or the standard deviation below 0.1, the cell trajectory is moved in this category as it is unsure if the trajectory is consistent.

Area: the cell falls within this category if the cell diameter is smaller than a certain threshold (10 for instance). This threshold is given in pixel and can be adjusted to object size and used equipment;

Tank treading: by exclusion, the cells passing through all the above criteria fall within the tank-treading category.

Part 2

After the automated step of Part 1, one can check and delete cells or confirm or move their categories.

For example, one can check that each cell is followed during a minimum amount of frames (set in the program). One can check as well that the cell displays no length change on the entire trajectory across the observation field of the microscope.

Second Experiment

In a second experiment, red blood cells were observed in brightfield microscopy (20× objective) along the direction of the flow gradient, at a distance h from the bottom wall of the chamber of less than 100 μm, i. e. in an area of constant shear rate. Videos of moving red blood cells passing through the camera field of view were taken with a camera that records the projected shapes of the cells in the plane perpendicular to the direction of the flow gradient.

Experiments conducted by observing RBCs located at a distance h=65 μm from the bottom wall of the chamber, under a shear rate of $\dot{\gamma}$=10 s$^{-1}$, were performed with a square field of view of length equal to 660 μm and the recording lasted at least one minute. The length of the field of view and the recording time enabled, for each experiment, to observe the motion of a number of RBCs ranging from 250 to 1200 and to detect the motion during at least half a period of tumbling/flip-flopping RBCs (with $\dot{\gamma}$=10 s$^{-1}$ and h=65 μm, the time T for a half rotation of a cell is 0.94 s and the distance L travelled by the cell is 613 μm). Movies were recorded at 21 fps with a camera and processed semi-automatically using Matlab home-made routines. The crossing time of the field of view of each RBC was 1.02 s, corresponding to 20 to 23 images recorded for each RBC. Using a custom-made «tracking and segmenting» Matlab program, each object present in a movie was individually tracked and a bounding box was defined around it to generate a sequence of 20-23 images saved in a separate file. The shape of the object detected in each image of a given sequence from the difference between the intensity of the grey levels of each pixel of the image was fitted by an ellipse.

Each sequence was analyzed using custom-made Matlab automatic programs and the RBCs animated either by a tanktreading or by a tumbling/flip-flopping/rolling motion (called other) were determined as follows:

Sequences where the major axis of the ellipse observed on each image constituting the sequence is smaller than 6 m are eliminated from the analysis. Indeed, it is then considered that the object detected is not an RBC but an artifact (debris, dust)

The remaining sequences are considered to be sequences showing RBCs.

If there are at least two images in the sequence for which the ratio between the minor axis and the major axis of the ellipse is less than 0.45, the RBC in the sequence is classified as 'other' (RBC viewed on the edge)

Figure 1:
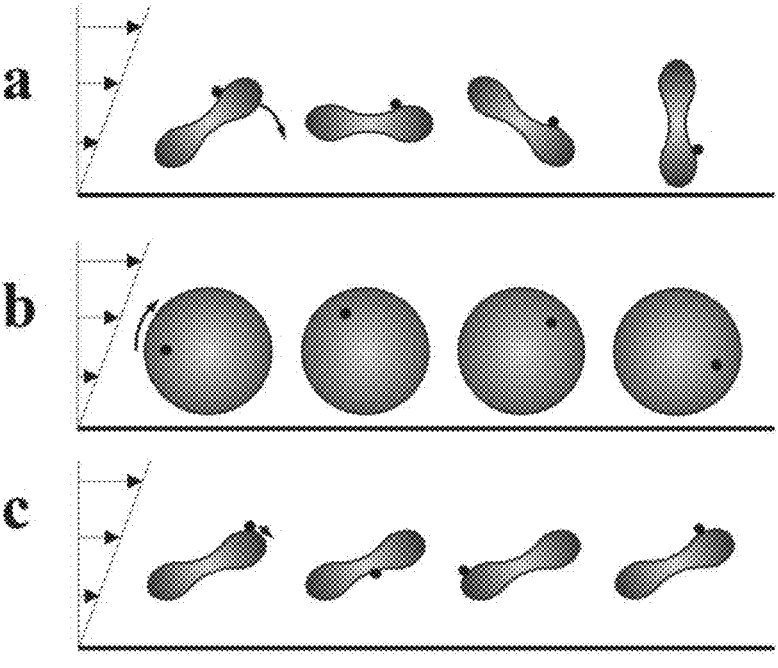
Figure 2:
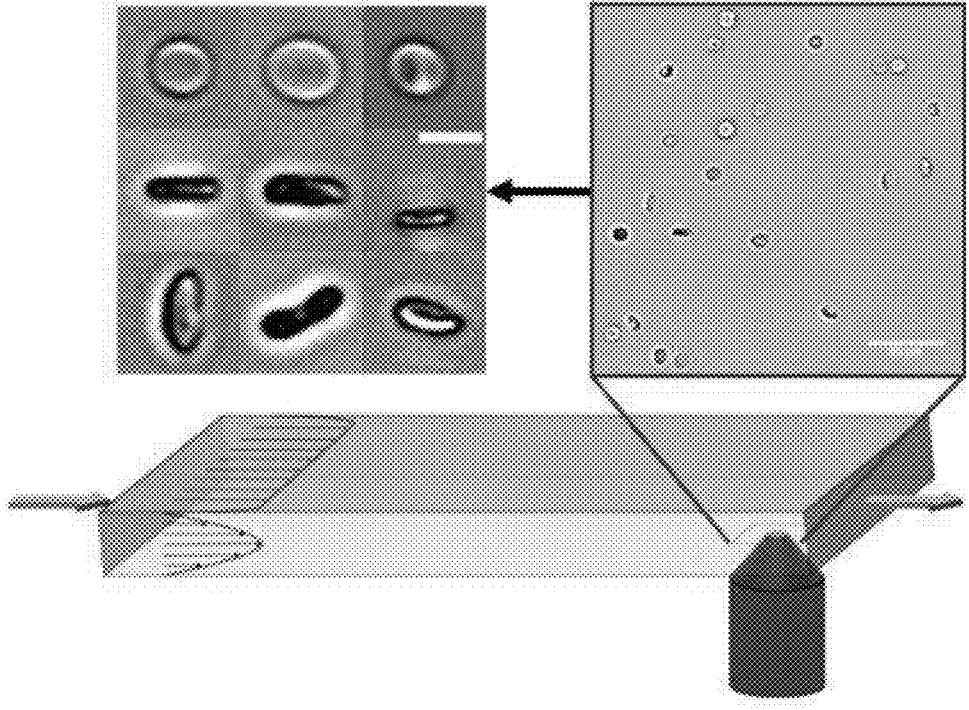

If all images in the sequence have ellipses with a ratio of minor to major axis greater than 0.45, the grey level intensity profile of each ellipse along the segment aligned with the flow direction passing through the centre of the ellipse and bounded by the contour of the ellipse is analysed. The RBC biconcavity (non-constant cell thickness) results in a grey-level intensity difference between the periphery and the centre of the cell (dimple) (FIG. 2 top, left images). Therefore, if the grey level intensity profile of 90% of the ellipses in the sequence has two extrema separated by at least 1 $\mu$m, the RBC is considered to maintain a stable orientation and therefore tank-treads. It is classified in the 'tank-treading' category. Otherwise the sequence is eliminated and the RBC is not counted.

For each shear rate, 250 to 1200 RBCs were observed and classified as tank-treading or other, and the fraction of tank-treading RBCs ($f_{TT}$) was calculated as the ratio of the number of cells classified as tank-treading to the sum of the number of cells classified as tank-treading and the number of cells classified as other.

Third Experiment

In another experiment, the RBCs were observed at a distance h=65 $\mu$m from the bottom wall of the chamber but were circulating at different heights in the flow chamber. Prior to the analysis of the sequences, it was necessary to eliminate the RBCs that were not in a layer located between 60 $\mu$m and 70 $\mu$m from the bottom of the chamber because the images of these cells were blurred and did not allow to determine the nature of the cell movements. Sequences with less than 20 images and more than 23 images were eliminated because they corresponded to RBCs circulating at a distance greater than 70 $\mu$m and less than 60 $\mu$m, respectively, and therefore blurred. The rest of the analysis was identical to the second experiment.

Statistics

For each shear rate, 250 to 1200 RBCs were observed and classified as tank-treading or not, and the fraction of tank-treading RBCs ($f_{TT}$) was calculated.

Results

The inventors focus on two diseases, mainly SCD, and to a lesser extent, thalassemia. The inventors also focus on two physical physiologically relevant quantities, often associated with painful SCD crises, namely RBC density and internal water content.

Figures 3A, 3B, 3C, 3D:
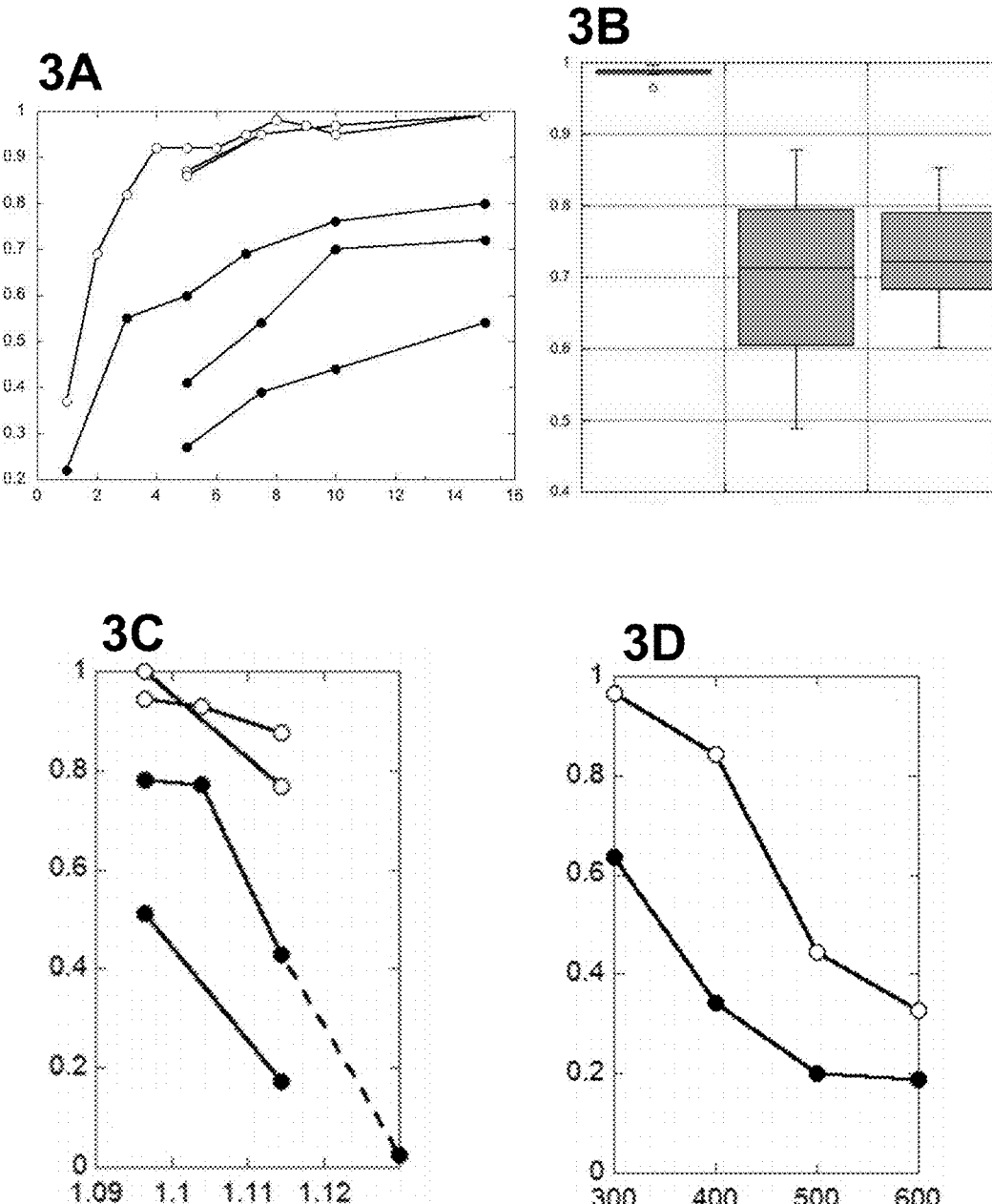

Transition to Tank-Treading Regime: Effect of RBC Density, Water Content and SCD The inventors observed the passage of collections of RBCs, including ISCs, (FIG. 2) and extracted the fraction of RBCs having reached the TT regime, which the inventors referred to as $f_{TT}$, as a function of the shear stress. As shown in FIG. 3A, the $f_{TT}$-increase with $\eta_o \dot{\gamma}$ exhibited two clearly distinct curves for healthy and SCD RBCs, thus suggesting that $f_{TT}$ could be a good candidate as a mechanical marker of SCD. The value of $f_{TT}$ measured at $\eta_o \dot{\gamma}$=0.6 Pa (i.e. $\dot{\gamma}$=15 s$^{-1}$) yields the strongest difference between the behaviour of SCD and healthy RBCs. The inventors chose this shear stress to characterize healthy and SCD RBC behaviours across many samples. At this shear rate, almost all HbAA RBCs (98.6±0.9%) are observed to be tank-treading versus only 70.4±12.9% for HbSS samples (FIG. 3B). The two distributions do not overlap, thus disclosing that $f_{TT}$ allows discriminating SCD from healthy RBCs. Moreover, the $f_{TT}$ distribution for HbSS RBCs is wide, revealing the heterogeneity of the mechanical properties displayed by SCD cells. Only 73.4±8.2% RBCs from heterozygotous thalassemic patients tanktread. This distribution does not overlap with that of the healthy RBCs, thus disclosing that $f_{TT}$ allows discriminating thalassemic from healthy RBCs.

Results from FIG. 3C show a marked decrease in $f_{TT}$ with cell density for both healthy and SCD samples. The $f_{TT}$ decreases with density is more drastic for SCD than for healthy RBCs.

Finally, $f_{TT}$ was found to be sensitive to RBC density and internal water content (figuring the state of dehydration of RBCs) as illustrated in FIGS. 3B and 3D. Here, RBC dehydration was achieved through hyper-osmolarity of the external medium, starting from the physiological 300 mOsm up to osmolarities of 600 mOsm. Results showed a marked decrease in $f_{TT}$ with cell density and dehydration for both healthy and SCD samples, the $f_{TT}$ decrease with density being more drastic for SCD than for healthy RBCs.

RBC dehydration is known to be a parameter relevant to the clinical condition of the sickle cell patient, favoring the occurrence of vaso-occlusive crises in SCD. Furthermore, the RBC density profile of SCD patients was shown to vary during vaso-occlusive crises. This suggested that $f_{TT}$ could be an easy-to-measure marker for questioning the clinical condition of a sickle cell patient during a vaso-occlusive crisis.

Fraction of TT RBCs as a Clinical Marker in SCD Crises

The inventors thus studied the temporal evolution of $f_{TT}$ on seven patients hospitalized for an acute SCD crisis as shown in FIGS. 4A and 4B. The first measurement, set at time=0, was done at the arrival of the patient at the hospital. In one case (patient HbSS 24), a measurement was done on the patient one week before he was admitted for an acute crisis. In another case (patient HbSS 20), the patient was admitted twice at the hospital for two crises that occurred two months apart. In two cases (Patient HbSS 23 and patient HbSS 21), the patients were hospitalized for a crisis and had another crisis during their stay at the hospital (FIG. 4B). Patient HbSS 23 was transfused at day 1, which, surprisingly, did not prevent the second crisis event. In all other cases of transfusion of patients, measurements were stopped after transfusion.

It clearly appears that $f_{TT}$ significantly varies during the course of the crisis. A maximum of $f_{TT}$ is typically observed. In general, this maximum is observed shortly after or shortly before hospitalization, as shown for patient HbSS 22, patient HbSS 19, patient HbSS 23, patient HbSS 21, and patient HbSS 24. The time at which this maximum is observed is taken in the following as the reference time at which the crisis occurs. In the case of patient HbSS 24, the maximum was probably reached before his/her late hospitalization but the value collected 7 days before the crisis allows highlighting the maximum during the crisis. Similarly, the maximum was probably also reached before hospitalization for the first crisis of patient HbSS 23 and patient HbSS 21. Patients HbSS 19 and HbSS 21 were monitored long enough after their crisis so that their $f_{TT}$ curves display a post-crisis decrease down to a constant level (base level). The two curves clearly show that this base level varies between patients, as already suggested by the strong dispersion of $f_{TT}$ measured on SCD patients (FIG. 3A). FIG. 4C pools all $f_{TT}$ curves shifted by subtraction of the base level to display the variation of $f_{TT}$ during a crisis, and shifted in time by defining the 0-time when $f_{TT}$ is at maximum. It shows that a variation between 6 and 10% is observed between the base level and the maximum of $f_{TT}$ reached during the crisis, and that $f_{TT}$ comes back to its base level within 2-3 days. Strikingly, a significant $f_{TT}$ decrease is observed several days before the crisis, that can reach 20% (patient HbSS 24) two days before the crisis. This shows that $f_{TT}$ is not only a relevant parameter of crisis but is also a crisis prediction marker.

Strikingly, $f_{TT}$ varies before and during vaso-occlusive events in SCD. The pre-crisis decrease is attributed to a larger number of RBCs with an enhance in membrane rigidity and/or in cytoplasmic viscosity. The strong increase in $f_{TT}$ during the crisis reveals that a large amount of these altered RBCs no longer circulate in the microvasculature, likely due to their lysis and/or their blockage in blood vessels. The blockage may be induced by an enhanced adhesiveness at the wall vessels and/or sequestration in clogged vessels. A strong asset of $f_{TT}$ is to be highly sensitive not only to the membrane rigidity, as it is the case for several methods, including ektacytometry, but also to cytoplasmic viscosity, a mechanical parameter that is strongly affected in SCD due to fibre formation of haemoglobin. Moreover, $f_{TT}$ is indirectly sensitive to RBC adhesiveness, a factor involved in vaso-occlusion, since HbSS non-deformable RBCs exhibit increased adhesion sites compared to HbSS deformable RBCs.

Evolution of the $f_{TT}$ Parameter on Patients During the "Out of Crisis" Period The inventors studied the variability of the $f_{TT}$ parameter on 9 homozygous SCD patients over 6 months. Each patient has been weekly tested and at least 10 times over the 6 months.

Patient 1 is a woman of 33 years old with kidney disease, and who is treated with hydroxyurea, converting enzyme inhibitor and folic acid.

Patient 2 is a woman of 48 years old with kidney and liver disease, and who is treated with hydroxyurea and IEC.

Patient 3 is a woman of 48 years old with liver disease and retinopathy, and who is treated with hydroxyurea.

Patient 4 is a woman of 35 years old who is untreated.

Patient 5 is a man of 45 years old with liver and kidney disease and retinopathy, who has deep vein thrombosis, and is treated with hydroxyurea, angiotensin converting enzyme inhibitor and antiplatelet agent.

Patient 6 is a woman of 24 years old who is treated with hydroxyurea and folic acid.

Patient 7 is a woman of 25 years old who has deep vein thrombosis, and who is treated with hydroxyurea.

Patient 8 is a woman of 35 years old who is treated with hydroxyurea.

Patient 9 is a woman of 23 years old who has deep vein thrombosis, and who is treated with hydroxyurea and who was treated with darbepoetin alfa from day 1 to day 15 and then with apixaban.

These patients did not suffer a vaso-occlusive crisis during the tested period. The mean $f_{TT}$ values recorded for each patient and the associated standard deviations are represented in FIG. 6. Temporal evolution of $f_{TT}$ per individual are displayed in FIGS. 7 to 15.

From FIGS. 7 to 15, it can be deduced that the difference between the $f_{TT}$ mean and the $f_{TT}$ values measured for each patient is less than twice the value of the standard deviation when patients do not have a vaso-occlusive crisis:

For patient 1, the mean $f_{TT}$ value is 0.805 and the standard deviation is 0.027;

For patient 2, the mean $f_{TT}$ value is 0.786 and the standard deviation is 0.035;

For patient 3, the mean $f_{TT}$ value is 0.840 and the standard deviation is 0.030;

For patient 4, the mean $f_{TT}$ value is 0.711 and the standard deviation is 0.050;

For patient 5, the mean $f_{TT}$ value is 0.853 and the standard deviation is 0.044;

For patient 6, the mean $f_{TT}$ value is 0.776 and the standard deviation is 0.057;

For patient 7, the mean $f_{TT}$ value is 0.724 and the standard deviation is 0.048;

For patient 8, the mean $f_{TT}$ value is 0.820 and the standard deviation is 0.070;

For patient 9, the mean $f_{TT}$ value is 0.658 and the standard deviation is 0.070.

Because in this example, the patients are heterogeneous in their diseases associated with SCD, in the treatments they receive, in their sex and age, and because for each of them the difference between the mean $f_{TT}$ value and each $f_{TT}$ value is less than twice the value of the standard deviation when they are not in crisis, it can be concluded that the $f_{TT}$ parameter is independent of the characteristics of these patients.

In addition, these results show that the $f_{TT}$ parameter is heterogenous and patient-dependent, but overall stable, with few fluctuations over time in the "out of crisis" period for each patient.

Evolution of the $f_{TT}$ Parameter in Patients in SCD Vaso-Occlusive Crisis

The inventors report in FIGS. 16, 17 and 18 the temporal evolution of $f_{TT}$ values in three patients who suffered vaso-occlusive crises during the period covered by the weekly follow-up study. Time sampling is complementary to that shown in FIG. 4. FIGS. 16 to 18 clearly show that each observed crisis is associated with a significant decrease in the $f_{TT}$ value during hospitalization.

For each patient, the mean $f_{TT}$ value and the associated standard deviation are calculated on the "out of crisis" period. For patient 10, the mean $f_{TT}$ value is 0,764 and the standard deviation is 0,035. For patient 11, the mean $f_{TT}$ value is 0,701 and the standard deviation is 0,049. For patient 12, the mean $f_{TT}$ value is 0.793 and the standard deviation is 0.038.

The results presented in these figures are in addition to those presented above in "Evolution of $f_{TT}$ parameter on patients in the "out of crisis" period", in that when the patient is in an "out of crisis" period, the difference between the $f_{TT}$ mean and each measured value is less than twice the value of the standard deviation for each patient.

In FIG. 16, the patient suffered from a first crisis period from day 109 to day 111, followed by a second crisis period begins after day 132 and ends before day 139, during which no measurements were made. The difference between the mean $f_{TT}$ and the value measured at days 109 and 111 is more than twice the value of the standard deviation.

In FIG. 17, the patient suffered from a crisis period from day 1 to day 2. Here too, the difference between the $f_{TT}$ mean and the values measured at day 1 and 2 is more than twice the value of the standard deviation.

In FIG. 18, the patient suffered from a crisis period from day 28 to day 30. Here again, the difference between the $f_{TT}$ means and the values measured at day 28, 29 and 30 is more than twice the value of the standard deviation.

For each patient, the lower $f_{TT}$ values are consistent with the patient's pain, a sign of the crisis.

Overall, these results show that the $f_{TT}$ parameter is very sensitive to vaso-occlusive crises with a significant decrease in the $f_{TT}$ value during a crisis that resulted in the patient's hospitalization.

The invention claimed is:

1. A method for in vitro determination of variation of deformability of red blood cells of a tested individual, the method comprising the steps of:

a) determining a first amount of red blood cells having a tank-treading motion in a population of red blood cells, said population of red blood cells being obtained from a sample of said tested individual, by performing the following steps:

i. subjecting the population of red blood cells to a flow within a circulation member having a boundary wall, the flow having a flow gradient and the boundary wall being perpendicular to the direction of the flow gradient, the flow having a direction and further having a wall shear rate from 1 s$^{-1}$ to 50 s$^{-1}$ and a viscosity from 10$^{-3}$ Pa·s to 10$^{-1}$ Pa·s, ii. recording in greyscale images, using a visualisation member connected to a recording member, motions and trajectories of at least a part of the red blood cell population in an observation field of the visualisation member and obtaining at least one video being a sequence of successive images of movement of the recorded red blood cells across the observation field, wherein the observation field is arranged perpendicularly to the direction of the flow gradient with a focus at a distance h where the flow has constant shear rate, wherein the images of the sequence comprise projected shapes of the red blood cells in a plane perpendicular to the direction of the flow gradient and parallel to the boundary wall of the circulation member, wherein the projected shapes of each red blood cell present a minor and a major axis, iii. individually tracking in all the images of the sequence of successive images the projected shapes relating to at least a part of the recorded red blood cells, obtaining a motion sequence of individual images for each red blood cell and determining for each projected shape of a particular red blood cell a grey level intensity profile from the greyscale images, iv. analysing evolution of the projected shapes of each tracked red blood cell in its motion sequence and classifying a motion type of the said each tracked red blood cell as follows:

(1) a red blood cell is classified as having a tank-treading motion on conditions that a ratio of the minor to major axis of its projected shape is greater than 0.45 in all images of its individual motion sequence and that the grey level intensity profile in at least 90% of its projected shapes has two extrema separated by at least 1 μm, (2) a red blood cell is classified as having another motion on condition that the ratio of the minor to major axis of its projected shape is less than 0.45 in at least two images in the sequence, v. determining the first amount as a ratio of the number of red blood cells classified as having a tank-treading motion to a sum of the number of red blood cells classified as having a tank-treading motion and the number of red blood cells classified as having another motion, wherein steps ii. to v. are implemented by a control module and performed automatically, b) calculating an absolute value of a difference between (1) said first amount of red blood cells having a tank-treading motion in a population of red blood cells, and (2) a second amount being a calculated mean of the determined amount of red blood cells having a tank-treading motion obtained in reference populations of red blood cells, said calculated mean of the determined amount being obtained along with a value of a standard deviation of the red blood cells having a tank-treading motion obtained in the reference populations of red blood cells, wherein said reference populations are obtained either from at least two independent samples of said tested individual, or from at least one sample of at least two individuals, said at least two individuals being different from said tested individual, c) determining said absolute value is greater than twice the value of said standard deviation d) concluding the red blood cells of said population present a significant variation of their deformability compared to the red blood cells of said reference populations.

2. Method according to claim 1, wherein the circulation member is a parallelepipedic flow chamber or a microchannel.

3. Method according to claim 2, wherein the observation field has a focus at most at 40% a height of the circulation member from the boundary wall.

4. Method according to claim 2, wherein the observation field has a length of at least a half period length L for enabling a red blood cell to show half a period of tumbling or a flip-flopping motion in the flow, L being determined according to the following formula:

$$L = 3 \cdot \pi \cdot h$$

wherein h is the distance of the focus of the observation field from the boundary wall of the circulation member.

5. Method according to claim 2, wherein the at least one video recorded at step ii. lasts at least a time T required for a red blood cell to perform a half-period of tumbling or flip-flopping motion in the flow, T being determined according to the following formula:

$$T = 3 \cdot \frac{\pi}{\dot{\gamma}}$$

wherein $\dot{\gamma}$ is the value of the wall shear rate of the flow.

6. Method according to claim 2, wherein the visualisation member comprises an objective with a depth of field, and wherein in step i. the red blood cells circulate in the circulation member in an extended layer centred at the distance h and of thickness corresponding to at most 5 times the depth of field of the objective.

7. Method according to claim 6, wherein in step i. the red blood cells are injected in the circulation member by a co-flow of two fluids configured to focus the red blood cells in the extended layer.

8. Method according to claim 2, wherein the visualisation member comprises an objective with a depth of field, wherein the recording member has an image frame rate of recording, wherein in step i. part of the red blood cells circulate in the circulation member in an extended layer centered at the distance h and of thickness corresponding to at most 5 times the depth of field of the objective, wherein in step i. the rest of the red blood cells circulates outside the extended layer, and wherein the method further comprises the following sub-steps for excluding from the analysis step iv. the red blood cells circulating outside the extended layer:

(1) counting the number of individual images constituting the motion sequence of each red blood cell, (2) excluding the red blood cells whose motion sequence has a number of individual images larger or smaller than N±1, wherein N∈ {0, 1, 2, 3, . . . }, wherein $$N = \frac{n \times L}{\dot{\gamma} \times h}$$

wherein n is the image frame rate of the recording member,

L is a length along the flow direction of the observation, $\dot{\gamma}$ is the shear rate of the flow, and h is the distance of the focus of the observation field from the boundary wall of the circulation member.

9. Method according to claim 1, wherein step iii. comprises a step of excluding from analysing step iv. any projected shape whose largest dimension is less than 6 μm.

\* \* \* \* \*